United States Patent [19]
Faller et al.

[11] Patent Number: 5,656,441
[45] Date of Patent: Aug. 12, 1997

[54] METHODS FOR DETERMINING CELLULAR ADHESION

[75] Inventors: Douglas V. Faller, Braintree; Irene Ginis, Brighton, both of Mass.

[73] Assignee: Trustees of Boston University, Boston, Mass.

[21] Appl. No.: 229,539

[22] Filed: Apr. 19, 1994

[51] Int. Cl.$^6$ .......................... C12Q 1/02; G01N 33/574
[52] U.S. Cl. .................. 435/7.21; 73/61.72; 435/7.2; 435/7.23; 435/7.24; 435/29; 436/56; 436/63
[58] Field of Search ............................ 73/61.72; 435/29, 435/240.23, 7.2, 7.21, 7.23, 7.24; 436/56, 63

[56] References Cited

U.S. PATENT DOCUMENTS

| | | | |
|---|---|---|---|
| 4,797,277 | 1/1989 | Arfors | 514/2 |
| 4,935,234 | 6/1990 | Todd, III et al. | 435/240.27 |
| 5,011,778 | 4/1991 | Newman et al. | 435/240.27 |
| 5,019,648 | 5/1991 | Schlossman et al. | 435/240.27 |
| 5,180,809 | 1/1993 | Ruoslahti et al. | 530/350 |
| 5,217,870 | 6/1993 | Hession et al. | 435/240.27 |
| 5,260,210 | 11/1993 | Rubin | 435/240.23 |
| 5,318,890 | 6/1994 | Rosen et al. | 435/7.24 |

FOREIGN PATENT DOCUMENTS 9011297  10/1990  WIPO.

*Primary Examiner*—David Saunders
*Attorney, Agent, or Firm*—James Remenick; Baker & Botts, L.L.P.

[57] ABSTRACT

This invention is directed to the measurement of distances between adherent particles and the surface to which the particles are adhered. The particles may be artificial such as beads or natural such as cells and are labeled with a detectable label. The surface may be a biological surface such as a cell, a membrane or a biological structure, or an artificial surface such as plastic or glass. The factor by which a signal emitted from particles adherent to the surface differs from the detected signal is directly related to a factor specific for each medium which can be calculated. Knowing this factor and the value of the amount of label detectable from the particles, the distance between the particle and the surface can be determined. Such methods can be used to monitor the degree of spreading of cells along a surface such as an extracellular matrix, to determine the physical nature of the cell surface, or to determine the nature of cell-to-cell and cell-to-ligand receptor bridges. These methods can also be used in testing surfaces such as tissue culture products for relative adhesiveness and in testing other products for overall stickiness or smoothness. These methods can also be used to screen chemicals, drugs, protein and many other substances to determine if they have an effect on cellular adhesion and spreading.

39 Claims, 8 Drawing Sheets

METHODS FOR DETERMINING CELLULAR ADHESION

BACKGROUND OF THE INVENTION

1. Field of the Invention

This invention relates to methods for determining the distance between particles and a surface to which the particles are adhered. Particles are labeled with a detectable label and adhered to a surface which may be a natural surface or an artificial surface. Label is detected from these particles under different conditions of adherence and a value is determined that reflects the strength of adherence. These methods are useful for determining the physical nature of a surface of any particle and surface phenomenon such as events associated with the cell adhesion, cell spreading and ligand-receptor interactions. These methods are so used for detecting and analyzing cell-associated pathological conditions and the physical nature of any surface.

2. Description of the Background

Cell adhesion to other cells and to biological surfaces is required for normal physiological processes such as leukocyte trafficking and the immune response, and is also an important factor in the development of pathological conditions associated with ischemia-reperfusion damage, autoimmune diseases and tumor metastasis. One of the principal cells in the adhesive process is the leukocyte. Adhesion of leukocytes involves specific interactions between complementary adhesion molecules present on both the leukocyte and endothelial surfaces. Subsets of leukocytes have different sets of adhesion receptors and each subset has different affinities and abilities to spread along endothelial cells (M. B. Lawrence and T. A. Springer, Cell 65:859–73, 1991; Y. Shimizu et al., Immunol. Today 13:106–12, 1992).

Stimulation of the inflammatory process is closely associated with control of the adhesive properties of leukocytes, endothelial cells and other cells. Cellular adhesion can be initiated or enhanced by inflammatory agents and other chemical inducers. For example, neutrophils can be activated with Fmet-leu-phe or phorbol esters such as phorbol myristic acetate (PMA). These agents and other chemical and biological inducers cause increased expression of adhesion molecules on cell surfaces, and potentiate adhesion, cell spreading and transendothelial migration (M. A. Arnaout et al., J. Cell. Physiol. 137:305–09, 1988; S. S. Smyth et al., Blood 81:2827–43, 1993). Activation of endothelial cells with IL-1, LPS or TNF produces increased expression of the endothelial cell adhesion ligands ICAM-1, VCAM-1 and ELAM-1, which also mediate strong adhesion of leukocytes (F. W. Luscinskas et al., J. Immunol. 146:1617–25, 1991; B. C. Hakket et al., Blood 78:2721–26, 1991).

Another particularly good example of adhesion is margination, the deposition of white cells within microvessels. As white cells tumble increasingly slowly along capillary and venule walls, the cells eventually come to rest and adhere to vessel endothelium. Damage can occur when the endothelium becomes lined with these cells. This phenomenon, not surprisingly, is referred to as pavementing and may be related to the development of arteriosclerosis and associated diseases.

Cells in culture mimic many types of adhesive behaviors and form specialized contacts between cells and with the extracellular matrix (ECM). These surface-to-surface interactions are believed to be identical to those formed in vivo (B. Geiger et al., J. Mol. Biol. 101:1523–31, 1985). Inflammatory mediators such as C3a, FMLP and LPS specifically stimulate increased expression and increased affinity of many of these proteins. Conversely, other inflammatory mediators inhibit adhesion and may serve to terminate inflammatory responses. The overall importance of these adhesion molecules is highlighted by a genetic deficiency, referred to as leukocyte adhesion deficiency, in which there is a deficiency in the $\beta$ and sometimes the $\alpha$ subunit. Patients with this disorder suffer from increased and recurrent bacterial and viral infections.

Many different families of proteins are important in cell-to-cell and cell-to-surface interactions. One group of adhesion molecules found on leukocytes is called the $\beta_2$-integrins and consists of a family of three glycoproteins LFA-1, MO-1 and p150/95. LFA-1, for example, participates in strong leukocyte-endothelial interactions, mediating firm adhesion, spreading and transendothelial migration (M. B. Lawrence and T. A. Springer, Cell 65:859–73, 1991; E. C. Butcher, Cell 67:1033–36, 1991). Structurally, these proteins are heterodimer complexes comprised of identical $\beta$ (beta) subunits and different $\alpha$ (alpha) subunits with a molecular weight range of 150,000 to 180,000 KDa.

Within this well studied family of integrins there are also specific cell surface proteins that mediate biological events involving cell-matrix and cell-cell interactions. The integrins provide a functional linkage between the extracellular matrix and the cells' interior providing a mechanism to effect cellular responsiveness to the extracellular environment. Some integrins also bind, and with great specificity, to a host of different types of ligands. Specificity is conferred by the subunit composition of the integrin complex. At least three major subgroups can be distinguished by the $\beta$ subgroup and six by the $\alpha$ subgroup. These protein complexes bind to extracellular ligands such as laminin, collagen and fibronectin, and to cytoskeletal proteins such as vinculin, talin and $\alpha$-actinin, via their cytoplasmic tails.

Integrins are an essential requirement for leukocyte adhesion and are also involved with functional activation of many cell types. Cellular adhesion requires a number of specific interactions which occur at the cell surface including podosomes, point contacts, dot contacts, focal contacts which may be uniformly distributed across the cell surface or localized at specific sites. Podosomes are large aggregates, on the order of 200–400 nm, which contain actin. Point contacts and dot contacts are smaller than podosomes, about 90–200 nm, and are closely apposed to the substratum of the cell. Focal contacts, or adhesion plaques are structures which traverse the plasma membrane linking the extracellular substrate with components of the cytoskeleton and contain concentrated amounts of integrin (K. Burridge et al., Ann. Rev. Cell Biol. 4:487–525, 1988). The ability of a cell to form focal contact correlates with its ability to assemble an organized cytoskeleton, a prerequisite to cell spreading and migration (E. Dejana et al., J. Cell Biol. 107:1215–23, 1987).

The early stages of cell attachment and spreading are believed mediated exclusively by integrins in point contacts. Unlike focal contacts, point contacts contain clathrin and rarely distribute with actin or vinculin. It has been proposed that different classes of adhesion molecules mediate the progression of weak point contacts to strong adhesion which results in spreading (E. C. Butcher, Cell 67:1033–36, 1991). In addition, strong adhesion and flattening or spreading is required prior to transendothelial migration of leukocytes (F. W. Luscinskas et al., J. Immunol. 146:1617–25, 1991; B. C. Hakket et al., Blood 78:2721–26, 1991). For example, the CD18 (cluster differentiation type 18) integrins, LFA-1 and MO-1, are thought to mediate strong adhesion, and antibodies against these integrins block strong adhesion, spreading and transendothelial migration.

Cellular adhesion is one of the many systems in which the presence of specific molecules is required for adhesion to occur (W. A. Frazier et al., *Cellular Recognition*, Alan R. Liss, Inc., New York, 1982). In both cell-to-cell and cell-to-surface adhesion, bridges are formed by adhesion molecules such as integrins and it appears clear that a substantial number of bridges must be formed to achieve successful adhesion. This later requirement indicates that there exists a repulsive barrier which must be overcome to permit adhesion to occur. The existence of a repulsive barrier is further supported by studies which show that even when numerous bridging molecules are present, cells must frequently be forced into close contact by centrifugation before strong bonding occurs.

There are many possibilities inherent in thermodynamic adhesion models. Each model can explain the thermodynamic considerations for a small number of cell surface interactions. None have been able to explain every type of interaction, however, a few general observations can be made.

First, specific bridging molecules, or receptors, become concentrated in regions of cell-cell or cell-substrate contact. Such accumulations of receptors in contact areas have been observed and can be deduced from the forces required to disrupt aggregates. Accumulations of receptors serve as transduction mechanisms for triggering cellular responses. This is demonstrated in the immune system in which activation, phagocytosis and exocytotic granular release have each been demonstrated to be controlled by contact. Redistribution of receptors could also serve as a signal for polarization of the cell membrane relative to the site of adhesion. Internal cell structural elements such as cytoskeletal elements, may be able to sense this polarization. If so the interior of the cell can also be polarized. Specialized cell-cell junctions such as synapses, tight junctions and gap junctions, could be the natural consequence of receptor accumulation in regions of cell-cell contact. Details of the junction to be affected are determined by specificities of the receptors and their interactions with each other and with other molecules of the cell.

Another observation is that there are many phase transitions in cell adhesion. The existence of these transitions makes it clear that adhesion cannot be thought of according to only the basic laws of mass action. Contact between cells can only be stabilized by highly cooperative rearrangements of the interval variables of the cells.

Theoretical models of cell-cell interaction predict that the distance between two adherent cells in the area of contact is determined by a balance between nonspecific repulsion of hydrophilic polymers associated with the cell surface, and attraction through specific ligand-receptor bridges (G. I. Bell et al., Biophys. J. 45:1051–64, 1984). The physical nature of cell-cell, ligand-receptor bridges depends on many parameters, such as the type of the receptors, the density and direction of a stress force, blockage of the receptors with monoclonal antibodies or transfer of adhesion mediators to different ligand-receptor pairs. The process of adhesion itself may represent a regulatable continuum with attachment being mediated by a single small contact point between an adhering cell membrane and a surface of adhesion, which progresses to a flattening or spreading of the adhering cell along the surface of adhesion, fostering multiple points of contact between the cell and the surface.

Adhesion is more than a simple sum of the independent contributions of the various attractive forces, but a thermodynamic interaction of the attractive and repulsive forces causing the overall free energy of the interaction to favor one configuration over many other possible configurations. Unfavorable configurations have a relatively strong repulsive barrier and a weak, if any, attractive force. Favorable configurations have, in addition to a counterbalanced repulsive barrier, a compilation of attractive forces which achieve a successful degree of bridging.

Direct correlations between adhesive properties and pathological sequelae has been demonstrated for a number of diseases and disorders. For example, tumor metastasis is a complex process involving dynamic interactions between tumor cells and extracellular structures. Stages of malignancy have been demonstrated in sublines of an epithelial cell strain using differences in adhesion to tissue culture plastic (J. G. Steele et al., J. Cell Sci. 100:195–203, 1991). Andre et al. compared ten human melanoma cell lines and identified independent measurable parameters which correlated adhesion with characteristics of transformed cells (Cell. Biophys. 17:163–80, 1990). Boxberger and Paweletz related the influence of various substrata on rat tumor cell morphology, motility and invasiveness (Anticancer Res. 10:741–51, 1990). Recently, Repesh et at. demonstrated that adriamycin-induced inhibition of melanoma cell invasiveness is correlated with decreases in tumor cell motility and increases in focal contact formation (Clin. Exp. Metastasis 11:91–102, 1993).

Connections between adhesion and disease are not limited to neoplasias. A specific inheritable defect in neutrophil motility has been traced to abnormalities in a 47 KDa and a 89 KDa proteins of the cytoskeleton (T. D. Coates et ah, Blood 78:1338–46, 1991). Patients with this defect have increased and recurrent infections. Platelet activation and abnormal adhesion has been shown to be involved with atherosclerosis (S. K. Peng et al., Artery 20:122–34, 1993). Cellular adhesion has been implicated in muscular dystrophy (J. Cell Sci. 97:149–56, 1990), demyelination-related disorders (Ann. New York Acad. Sci. 605:1–14, 1990), and prostatitis (Urol. Int. 46:15–17, 1991). Furthermore, cellular adhesive properties have obvious importance in cell attachments to implants such as osteoclast attachments to a dental matrix (C. Wedenberg and S. Yumita, Endod. Dent. Traumatol. 6:255–59, 1990) and the formation of focal contacts by osteoblasts on orthopedic biomaterials (D. A. Puleo and R. Bizios, J. Biomed. Mater. Res. 26:291–301, 1992).

The development of reagents designed to prevent cell adhesion and pathological sequelae is being actively pursued for many of these pathological conditions. Anti-integrin antibodies have been identified that stimulate specific integrin function (K. M. Neugebauer and L. F. Reichardt, Nature 350:68–71, 1991; B. M. C. Chan and M. E. Hemlet, J. Cell Biol. 120:537–43, 1993). Whether this has more to do with increased expression or increased activation is not dear, but what is clear is that there are many agents which can effect, either directly or indirectly, the process of adhesion. Key features of this process, and certain pathological consequences, include adhesive interactions between minor cells and extracellular matrix components and enzymatic degradation of components. Properties such as invasiveness, growth, differentiation and motility are dependant to some degree on the adhesive properties of the tumor cells (L. A. Liotta et al., Cell 64:327–36, 1991). These properties have been ignored as a diagnostic means because there has been no accurate, reproducible and inexpensive method to measure cell surface distances.

SUMMARY OF THE INVENTION

The present invention overcomes the problems and disadvantages associated with current strategies and designs and provides new methods for measuring particle to surface separation such as cell-to-surface, cell-to-cell and cell-to-ligand distances which allows for characterization of events related to cell adhesion and adhesive mechanisms, cell spreading, ligand-receptor interactions and other cell surface phenomenon. Cell-to-cell and cell-to-surface separation distances relate to the physiological condition of a cell or tissue and allow for physiological analysis of both normal and pathological conditions. The invention further allows quantitative and qualitative measurements of the adhesive properties of particles and surfaces, either of which may be pre-treated to affect adhesive properties.

One embodiment of the invention is directed to methods for measuring cellular adhesion in a population of cells. Cells are labeled with a detectable label and suspended in a liquid medium. Suspended cells are divided into a plurality of wells wherein each well contains a comparable number of cells and a different volume of medium. Label is detected from the wells and a function of the amount of label detected verses the volume of medium per well calculated. Using this function, a quenching factor ($K_H$) of the medium can be determined. Cells are adhered to a surface of the wells and label detected again from the wells of adhered cells. Using the quenching factor previously determined and the amount of label detected from the adhered cells, adhesion in the population of cells can be measured both qualitatively and quantitatively. Measurements are useful for detecting diseases and disorders, for studying the effects of various treatments and compositions on cells and for analyzing events which occur at the cell surface.

Another embodiment of the invention is directed to methods for determining distances between cells and a surface to which the cells are adhered. Cells are labeled with a detectable label and suspended in a liquid medium. A portion of the population is divided into a plurality of wells wherein each well contains a different number of cells and a comparable volume of medium. Optionally, cells may be adhered to the well surfaces. Cells are lysed, for example, with a detergent, and the amount of label again detected. The amount of label emitted from the cells is detected and recorded. Using the mount of label detected, a function of cell number verses label detected can be determined and used to calculate a quenching factor of the medium. Another portion of cells is divided into another plurality of wells, adhered to well surfaces and the mount of label again detected. Using the quenching factor of the medium previously determined and the amount of label detected from the wells of adhered cells, the distance between the adhered cells and the well surface can be determined. This value can be represented as percent of ideal flattening.

Another embodiment of the invention is directed to methods for determining the size of a bound ligand/receptor interaction on a cell surface. A population of cells possessing surface receptors is labeled with a detectable label and suspended in a liquid medium. A portion of the suspension is divided into a plurality of wells and the cells adhered to well surfaces. Label is detected from the plurality of wells and the mounts recorded. Ligand is added to another portion of the suspended cells and bound to the cell surface receptors. Cells are divided into another plurality of wells and adhered to well surfaces. Label is detected from the plurality of wells containing bound cells and the size of the ligand/receptor interaction determined by comparing the mounts of label detected from the ligand bound and the unbound cells.

Another embodiment of the invention is directed to identifying a treatment that effects an adhesive property of a population of cells. Cells are labeled with a detectable label and suspended in a liquid medium. A portion of the suspension is divided into a plurality of wells and the cells adhered to well surfaces. Label is detected from the adhered cells and the mount of adhesion determined. Another portion of suspended cells is subjected to the treatment or process suspected of affecting adhesion. The treated cells are divided into another plurality of wells and the cells adhered to well surfaces. Alternatively, well surfaces may be treated and the suspended cells adhered to treated well surfaces. Label is again detected and the amount of adhesion which occurs with the treated cells determined. The values obtained for treated and untreated cells are compared to identify whether and how the treatment effects cellular adhesion. Treatments identified as affecting cellular adhesion include thermal treatments, treatments with electromagnetic radiation, chemical treatments and treatments whereby cells are exposed to a pharmaceutical composition.

Another embodiment of the invention is directed to methods for determining the adherence of a surface. A population of particles, such as beads, are labeled with a detectable label and suspended in a fluid medium with a known or determinable quenching factor. The fluid medium may be a liquid or a gas. The particles are adhered to the surface to be tested and the mount of label detected. Using the quenching factor and the mount of label detected, the adhesiveness of the surface can be determined. Surfaces to be tested may comprise ceramics, glasses, plastics, metals or biological membranes. These surfaces can also be treated before testing to determine the effect of a treatment process on surface adhesiveness.

Another embodiment of the invention is directed to compositions comprising an agent which affects cellular adhesion and a pharmaceutically acceptable carrier. Compositions are useful to treat or prevent disorders that relate to cellular adhesion in humans and other animals.

Another embodiment of the invention is directed to methods for treating a disorder in a patient by interfering with cellular adhesion. Treatments may involve therapeutic or prophylactic procedures or compositions which affect cellular adhesion. Disorders which can be treated include inflammations, infections, neoplasias, diseases of the hematopoietic system, diseases of the immune system, cardiac diseases and genetic defects and deficiencies.

Another embodiment of the invention is directed to methods for measuring adhesion of particles to a surface. Particles are labeled with a detectable label and suspended. The suspended particles are divided into a plurality of samples wherein each sample contains a different number of particles in a comparable volume. Label is detected and the function for label detected verses particle number calculated to determine a quenching factor. Particles are adhered to the surface and label is again detected to measure the adhesion of particles to the surface. These methods are useful in the manufacture and quality control of tissue culture plates and other products with defined and reproducible adhesive properties.

Other embodiments and advantages of the invention are set forth, in part, in the description which follows and, in part, will be obvious from this description or may be learned from the practice of the invention.

DESCRIPTION OF THE INVENTION

Figure 1A:
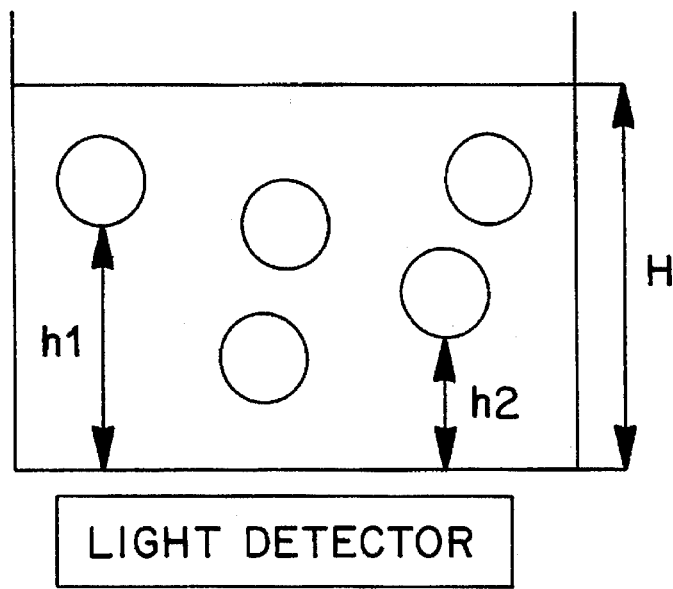
FIG. 1 Schematic comparison of the distribution of A suspended cells and B ideally flattened cells in a microtiter well.

As embodied and broadly described herein, the present invention comprises rapid and quantitative methods for determining the distance between a population of particles, which may be a collection of beads or cells, and an artificial or biological surface to which the particles are adhered. Physical and biological events which occur at the cell surface can be quantitatively determined including the physical nature of the adhering surface. These methods are based on the observation that, using labeled particles, the medium between the particles and the surface of adhesion absorbs or attenuates an emitted signal otherwise detectable from the adherent particles. No similar methods have been described which permit routine quantitative estimation of the degree of spreading on artificial or biological surfaces. Further, the process is simple, inexpensive, rapid and quantitative, and can be performed simultaneously on many samples. It is more sensitive than visual observation of particle or cell morphology and allows one of ordinary skill to characterize particle-surface separation distances which can not be observed by light microscopy.

One embodiment of the invention is directed to a method for measuring cellular adhesion in a population of cells. Measurements are useful for detecting diseases and disorders, for studying the effects of various treatments and compositions on cells and for analyzing events which occur at the cell surface. Pathological conditions which can be detected are those in which there is a measurable change in the adhesive properties of a population of cells to a biological or artificial surface. Detectable conditions include inflammations, infections, neoplasias, hematopoietic system disorders, cardiac diseases, immune system disorders, apoptosis and genetic defects and deficiencies. Some of the more common cardiac and inflammatory disorders detectable include atherosclerosis, arteriolosclerosis, arteriosclerotic and syphilitic aneurysms, ischemia-reperfusion injury and other diseases of the heart and its vessels. Neoplasias may be especially susceptible to detection by these methods as neoplastic cells represent an altered cellular state with coincident altered morphology, surface expression and surface conditions. Some of the more common neoplasias which can be detected include leukemias, lymphomas, sarcomas, carcinomas such as squamous cell carcinomas, neural cell tumors, seminomas, melanomas, germ cell tumors, undifferentiated tumors, neuroblastomas, mixed cell tumors, metastatic neoplasias, neoplasias caused by infections such as viruses (e.g. human papilloma virus, Cytomegalovirus, Herpes Simplex virus I or II, hepatitis virus, human T cell leukemia virus or another retrovirus) or another malignancy. Neoplastic diseases of the immune system which can be detected include the non-Hodgkin's lymphomas including the follicular lymphomas, Burkitt's lymphoma, adult T-cell leukemias and lymphomas, hairy-cell leukemia, acute myelogenous, lymphoblastic or other leukemias, chronic myelogenous leukemia, and myelodysplastic syndromes. Additional neoplastic disorders which may be specifically detectable include breast cell carcinomas, melanomas and hematologic melanomas, ovarian cancers, pancreatic cancers, liver cancers, stomach cancers, colon cancers, bone cancers, squamous-cell carcinomas, neurofibromas, testicular cell carcinomas and adenocarcinomas.

Adhesion can also be used as an indicator of cell activation or deactivation, to detect the metastatic potential of a cell, to detect a malignant or benign state or a state of transformation, or to detect and measure an increased or decreased metabolic activity. Cell labeling and adhesion assays may further be used to monitor cell functions such as gene expression, membrane potential, cytoplasmic pH levels and levels of intracellular chemicals and proteins and, together with measurements of cell-surface separation distance, allow for correlation of these parameters with effects on cell spreading, attachment or lack of attachment, differentiation and morphology.

Cells in which there can be a detectable change in adhesion include circulating cells and cells of the hematopoietic system such as leukocytes, neutrophils, peripheral blood lymphocytes including B and T cells, monocytes, macrophages and erythrocytes, transformed cells such as human leukemia cells and other neoplastic cells, and immortalized cell lines such as Jurkat cells, human T cell leukemia cells and JY cells, and Epstein-Barr virus transformed cells. Tissues and other macromolecular structures which comprise cells may also be sampled and the cells removed for testing. This includes endothelial cells, cells of the major and minor organs such as the heart, liver, prostate, spleen, lung, gastrointestinal tract including the stomach, colon and small and large intestines, pancreas and skin.

Cells tested are preferably human, or derived from another mammal, and may be obtained from surgical biopsy, serum and other liquid samples, cervical puncture or by other means convenient for harvesting a particular cell type. Cells to be tested may be purified or partially purified, or used as heterogeneous mixtures of cells. When testing mixtures, results will reflect the overall adhesion and spreading of the mixture. Known values can be subtracted or the mixture may be reflective of a similar mixture in vivo. Where appropriate, test cells or controls may be of the same or of a similar cell-type to those tested and may be from the same or a different patient or source.

For testing, cells are labeled with a marker which can be detected visually with natural, infrared or ultraviolet light, by emission of a detectable signal such as decay particles from radioactive isotopes ($\alpha$ or $\beta$ decay particles), or by visible or invisible radiation such as fluorescence, phosphorescence or luminescence. Suitable labels are preferably nontoxic and include florescent chemicals such as calcein or ethidium bromide, luminescent chemicals, chromatic chemicals, bioactive chemicals, detectable metals and alloys, radio isotopes such as $^{32}P$, $^{35}S$, $^{3}H$, $^{125}I$ or $^{14}C$, stable isotopes and combinations thereof. Labels may also be organic or inorganic dyes or resins which can be detected with a commercially available detector. Labeling may be performed by incorporation of the chemical or chemical compound naturally through diffusion (e.g. calcein), intercalation (e.g. ethidium bromide) into cellular components, active metabolic uptake (e.g. radiolabeled saccharides), conjugation to a surface receptor either specifically or nonspecifically, or enzymatically using, for example, radiolabeled amino acids or nucleosides. Label may also be selectively detectable only after cells are subjected to an outside influence such as electromagnetic radiation. For example, exposure to visible light will excite certain phosphorescent chemicals to emit rays of visible light which can be easily detected. Types of electromagnetic radiation which will excite and render selected chemicals detectable include gamma rays, x-rays, ultraviolet rays, visible light, infrared rays, microwaves, radio waves, electric fields and combinations of these waves and rays.

Because the chemicals used are preferably non-toxic for the cells, it is another advantage of this procedure that measurements of cell spreading can also be employed before, during or at the end of any routine assay. Optionally, medium may be supplemented with chemicals whose absorption spectrum overlaps the spectrum of emitted label. This will increase the value of the extinction coefficient, and thus, all calculations will be increased and may result in increased accuracy of all measurements.

Testing may be performed on cell populations which are initially suspended or alternatively adhered to a surface or to each other in a liquid medium. Adherent cells such as tissues can be teased apart by, for example, physical manipulations, mild trypsinization or ionic treatments. These cells are suspended in medium and allowed to adhere under testing conditions. Suitable liquid medium for testing is liquid is which cell viability, or at least integrity, is maintained for the duration of the testing period. Examples of useful types of liquid media include cell culture medium, saline such as phosphate buffered saline, ionically balanced solutions or combinations thereof. Cell suspensions contain generally between about $10^3$ to about $10^8$ cells per ml, and preferably between about $10^4$ to about $10^7$ cells per ml, depending partly on the size of the cells in relation to the detectability of the label, and for most cells is preferably between about $10^5$ to about $10^6$ cells per ml.

The suspension is divided into a plurality of wells. Wells may be any type of receptacles for holding fluid such as the wells formed on a microscope slide, coverslip or tissue culture product, but are preferably wells of a microliter plate. Tissue culture products including dishes, microtiter plates, roller bottles, ampules, glass slides or coverslips may be coated with cell monolayers or chemical or biological substances which encourage or enhance adhesion such as fibronectin, vitronectin, collagen, laminin or combinations of substances. Use of coverslips permits measurement of the spreading parameter in practically any adhesion system, including flow chambers.

A detector suitable for measuring the label is placed near the wells of cells and an amount of label detected determined (F suspended or Fsusp). When using a microtiter plate, the detector is typically placed under the plate and in very close proximity to one well at a time. Each well is read for a preset time period and the detector advanced to the next well in a rapid, ordered fashion. Commercially available detectors include the CytoFluor 2300 Plate Scanner (Millipore; Bedford, Mass.) for fluorescent labels, gamma or scintillation counters for radioactive labels and spectrophotometers or ELISA plate readers for visually detectable labels. These detectors can be used to perform automated testing.

In a fixed volume of medium, the label detected from a single cell or population of cells in suspension is dependant upon the extinction properties of the medium and upon the distance between the cells and the detector. Measuring the label detected from wells containing a constant number of cells, but different volumes of medium can be represented as a function of label detected verses well volume. This function can be solved using curve fitting algorithms, such as least squares analysis for substantially linear functions, to determine the theoretical absolute amount of label loaded into a specific number of cells at any volume. Alternatively, suspended or adhered cells may be lysed and the amount of label detected measured again (Fsusp) to imitate the condition when the same amount of cells would be suspended a certain volume. Cell lysis may be performed by the addition of an anionic detergent (e.g. sodium dodecyl sulfate (SDS)), a cationic detergent (e.g. benzalkonium chloride), a zwitterionic detergent (e.g. CHAPS), or a non-ionic detergent (e.g. Tween 20 and Triton X-100). Detergents are used to produce a final concentration in the range of about 0.0001% to about 10%, preferably between about 0.01% to about 1.0%. Cells may also be lysed by changing the pH of the medium with, for example, a small amount of a strong alkaline such as sodium hydroxide to raise the pH of the solution to greater than about 8.5. The lysing agent should have a minimal effect on measurements or should be controlled for with positive and negative controls. Alternatively, cells may be lysed by simple physical disruption using a device to break cell membranes. This sort of agent need not be accounted for in calculating measurements as it can be introduced to and removed from wells as necessary. Lysis releases virtually all of the label into suspension and decreases the amount of label detected.

Accounting for the distance between the well and the detector, the quenching factor ($K_H$) of the medium, is directly proportional to the extinction coefficient (E) o the medium and can be determined for most any label (fluorescence, luminescence, radioisotope, etc.), most any volume of media ($K_{100}$ for 100 uls, $K_{200}$ for 200 uls, etc.), and most any type of medium (saline, cell culture medium, ionically balanced solutions, etc.). It does not depend on cell number, cell size or the amount of label in the cells and relates the amount of label detected from cells to the genuine or absolute amount emitted by these cells, and remains the same even if cells are lysed and label released into the medium. As $K_H$ is defined only by the extinction properties of the medium and the volume of the cell suspension in the well, it can be represented by the formula:

$$K_H = \frac{1 - e^{-EH}}{EH}$$

Although an adherent cell is much closer to the bottom of the plate, and thus, to the detector than a suspended cell, it is not still an ideally flattened cell. There is some distance between the adherent cell and the surface of adhesion. This distance depends on parameters, such as on the degree of cell spreading or flattening upon the surface, or on cell-surface separation distance. If a solution of, for example, light-absorbing absorbing reagent fills the space between adherent cells loaded with fluorescent dye and a surface of adhesion, the fluorescent light emitted by the cells will be quenched. Knowing the quenching factor ($K_H$) for the cells in suspension, an analogous calculation for adherent cells can be determined. This factor is referred to as the percent of ideal flattening (PIF). PIF is a percent ratio of the detected fluorescence of adherent cells (F adherent or Fadh) to the absolute emitted fluorescence of these cells (Fo) which takes the extinction coefficient into account. These values are related by the equation:

$$PIF = \frac{Fadh}{Fo} \times 100\%$$

With the value of $K_H$ known, Fo can be determined and Fadh is obtained directly. Another portion of suspended cells is divided into another plurality of wells and the cells adhered to a surface of the wells. Cells can be adhered, for example, by gravity by allowing the cells to settle out of suspension over a short period of time. Settling generally occurs between about 5 minutes and about one hour, but preferably less than about 30 minutes. Adherence can also be encouraged by gentle centrifugation of the well or plate, or by coating the well with adhesion promoting substances such as cells, fibronectin, vitronectin, collagen, laminin or combinations thereof. These substances increase the number of attachment sites and promote adherence. If necessary, nonadherent cells can be removed with washes of media, PBS or another salt solution, or by upside down centrifugation of the plates. The amount of detectable label remaining after centrifugation is measured and related to initial label of, for example, plated cells. Adhesion properties of adherent cells depends on the strength or affinity of adhesive interactions and on the number of these interactions. Strength can be characterized by the centrifugation forces cells are capable of withstanding. Application of different centrifugation forces with different strengths will result in the adherent cell populations interacting with the adhesive surface with different strengths corresponding to the detachment forces applied. Saturation of the interactions of the particular strength is accomplished by the addition of increasing numbers of plated cells per well and centrifugation at the particular speed or force. Increased numbers of plated cells and thus increased amounts of detectable label from these cells does not result in increase of the number of adherent cells remaining in the wells after centrifugation when all interactions of particular affinity are saturated. The amount of label detected from the adhered cells (Fadh) is measured using a detector appropriate for the label such as a fluorescent scanner for fluorescently labeled cells. Label intensity is a function of the distance between the cells and the bottom of the plate's inner surface. Using Fadh determined, Fo and $K_H$ calculated, absolute or relative distances between cells and surfaces to which the cells are adhered can be accurately determined.

The amount of label detected is directly related to the volume of the well and the $K_H$ of the medium. With the value for Fadh known and the value for Fo determined from Fsusp and $K_H$, a value for PIF can be determined.

$$Fo = \frac{Fsusp}{K_H} \quad PIF = \frac{Fadh}{Fo}$$

For most purposes, relative measurements of cellular adherence are most easily determined and PIF values are sufficient, but absolute distances can also be determined by utilizing algorithms or comparative examples having a known distances. Knowing the PIF values for the controls and determining the PIF value of the unknown, it is a straight forward matter to determine the absolute value for the cellular distance of the unknown. These calculations, with either relative or absolute results, allow for very accurate determinations of changes in the distance between cells and any artificial or biological surface, and for observation as to how this distance changes in real time as different factors are introduced into the system.

Measurements can be used to monitor the degree of spreading of, for example, human neutrophils on endothelial cells or on extracellular matrix protein-coated surfaces. Quantitative changes of this parameter are observed after neutrophil or endothelial cell activation and in the presence of monoclonal or polyclonal antibody directed against neutrophil integrins. Spreading measurements are more sensitive than visual observation of neutrophil morphology on surfaces or endothelial cells, and further, assays are easily modified for use in different sizes and brands of microtiter plates and different types of labels in the medium. Results are also helpful for diagnosis of pathological states when adhesion interactions are partially altered and have to be dissected from overall adhesion mechanisms.

Many different cell surface changes or phenomenon can be measured using this same process including changes in surface-to-surface distances in response to pharmacological agents and various extracellular or intracellular conditions, and the relative or absolute sizes of ligands, antigens, antibodies, receptors or complexes which attach to or form on the cell surfaces. In addition, the qualities of different surfaces to mediate spreading and the distinction between different adhesion receptor/ligand pairs participating in the adhesion process can be measured. This method also permits fine and quantitative measurements of the effects of monoclonal antibodies against specific adhesion receptors on cell-surface separation distance rather than on overall cell adhesion. The simultaneous testing of different cell functions, which may also utilize a detectable label, such as membrane potential, cytoplasmic pH, intracellular $Ca^{2+}$ and actin concentrations, together with measurements of cell-surface separation distance allows for a correlation of these parameters with effects on cell spreading, attachment or lack of attachment, differentiation and morphology.

Another embodiment of the invention is directed to a method for determining a size of a ligand/receptor interaction on a cell surface. A population of cells containing surface receptors, such as a population of circulating cells, cells of the hematopoietic or immune systems or immortalized cell lines, is labeled with a detectable label, such as those described above, and suspended in an appropriate liquid medium. Specific cells types which can be used include neutrophils, monocytes, peripheral blood lymphocytes including B and T cells, erythrocytes, endothelial cells, epithelial cells, fibroblasts, cell lines such as Jurkat cells, human T cell leukemia cells, Epstein-Barr virus transformed B cells or other tumor cells.

A portion of the suspended cells is divided into a plurality of wells, such as wells of a microtiter plate, and the cells adhered to a surface of the wells. Adherence may be promoted or enhanced by coating the wells and the amount of label detected from the first plurality of wells is measured and recorded. Ligand is added to another, second portion of suspended cells, and becomes bound to the cell surface receptors such as by incubation over time with constant physical agitation of the mixture. The ligand bound cells are divided into another or second plurality of wells and the cells adhered to a surface of the wells in a similar fashion to the first. Alternatively, ligand may be coated to well surfaces and the second portion of suspended cells added to these wells. Label is detected from the second plurality of wells and the size of the ligand/receptor interaction determined from a comparison of the label detected from bound and unbound cells, and thus, the measurements of cellular adhesion for each. From, the comparison and possibly a further comparison to controls with known distance-PIF correlations, the size of the ligand-receptor interaction and the physical structure of the cell surface can be determined.

Ligands which may increase or decrease cellular adhesion include enzymes, cytokines, recombinant gene products and combinations and fragments thereof such as fusion proteins, and ligand-receptor complexes such as antibody-antigen complexes. The antibodies used may be polyclonal or monoclonal, may be fragments of antibodies such as Fab fragments, and may be of any class including the human classes $IgG_1$, $IgG_2$, $IgG_3$, $IgG_4$, IgM, $IgA_1$, $IgA_2$, IgD and IgE, and combinations thereof. In addition, effects of the agents at the cell surface which do not bind, but alter surface morphology may also be measured in a similar fashion.

Another embodiment of the invention is directed to a method for determining the effect of a pre-treatment on the adhesive properties of a population of cells. Adhesion is measured as described for both treated and untreated cells. Comparison of the results achieved indicates the effect or consequence of the pre-treatment on adhesion. Pre-treatment process which can be utilized include radiation, heat and chemical treatments, treatments with a pharmaceutical composition, enzyme or cytokine, or combinations of these treatments. Comparisons of the effect of pre-treatments on similar cell types such as cells of the same genus, species, tissue-type, disease state, maturity or passage number, will provide results which can be utilized to classify the treatment as useful for effecting particular diseases or disorders such as hematopoietic or immune system disorders, cardiac diseases, genetic defects and deficiencies, infections and neoplasias.

Another embodiment of the invention is directed to a method for identifying an agent, process or condition that affects cellular adhesion. Cell are obtained, for example, from diseased or normal tissue of a patient, labeled with a detectable label and divided into a first portion and a second portion. The first portion is divided into a first plurality of wells and the cells adhered to a surface of the wells. Label is detected from the wells and a value for the mount of cellular adhesion of the first portion of cells determined. The second portion of cells is treated with the agent, process or condition suspected of having an effect on cellular adhesion to form a treated mixture. The mixture is divided into a second plurality of wells and the cells adhered to a surface of the wells. Alternatively, well surfaces may be treated and the cells adhered to treated well surfaces. Label is detected from the wells and a value for the amount of cellular adhesion of the mixture determined. From a comparison of the values for cellular adhesion in the presence and absence of the affecting agent, process or condition, it can be determined whether there had been any effect on cellular adhesion. Agents which are expected to effect cellular adhesion include antibodies, antibody fragments, synthetic and biological chemicals, liposomes, synthetic and natural particles, cells such as endothelial cells, membranes, proteins, carbohydrates, cytokines and many chemotherapeutic agents which alter cellular metabolic activity or differentiation. These agents or combinations of these agents may be coated to well surfaces or interacted with cells in suspension or adhered to surfaces. Processes and conditions which may effect cellular adhesion include thermal (heat or cold) treatments, exposure to chemicals such as oxygen radicals (e.g. ozone), oxygen radical scavengers (e.g. ascorbic acid), electromagnetic radiation including visible light at various wavelengths, vitamins, treatment with various pharmacological composition or therapies for the treatment of certain diseases and disorders. The results obtained can be used as a screening or testing process to determine the identities or functions of the various agents. and processes. Such applications can be useful in both the identification of pharmaceuticals and the manufacture of products with defined surface properties.

Another embodiment of the invention is directed to a composition comprising an agent that affects cellular adhesion and a pharmaceutically acceptable carrier. The agent may be previously unknown or known, but not previously recognized as useful as a regulator of adhesion. The agent may be identified by the above process or a similar process. The agent may be purified, semi-purified or mixed with other agents or compositions which have related or distinct effects on the patient. Useful pharmaceutically acceptable carriers include water, saline, alcohol, polyethylene glycol, oil, polysaccharides, salts, glycerol, stabilizers, antioxidants, emulsifiers and combinations thereof. Carriers allow for the agent to be introduced into the patient while ensuring suitable bioavailability and stability both in the patient and on the shelf.

Another embodiment of the invention is directed to a method for treating or preventing a disorder in a patient by interfering with cellular adhesion of diseased cells. Disorders which may be treated by this method include inflammations, infections, neoplasias, heart diseases, diseases of the hematopoietic system, premature apoptosis and genetic defects and deficiencies, and are preferably human disorders. Agents, previously identified as affecting cellular adhesion and treating or preventing a disorder are administered to the patient. Administration may be by parenterally, sublingually, rectally or enterally routes as convenient or appropriate to treatment. Direct injection into a vein or artery is preferred for systemic effects, but direct application to the area of the body to be affected may also be possible. These methods may be coupled with other, more traditional forms of therapy such as chemotherapy, immune therapy or radiation therapy as necessary for patients.

Another embodiment of the invention is directed to a method for determining adherence of a surface. A collection of particles is labeled with a detectable label. Particles may be artificial, such as beads of latex, saccharides or other polymers, or crystals of metals or alloys, or biological such as living or artificial cells, liposomes, vesicles or other lipid membranes. Preferably the particles are uniform to increase the accuracy of measurements. As the purpose is testing of the surface, inexpensive and readily available particles are also preferred. Particles are labeled with a detectable label and suspended in a fluid which may be a liquid, a gas or a near vacuum. Useful labels include florescent chemicals, luminescent chemicals, phosphorescent chemicals, chromatic chemicals, metals, radio isotopes, stable isotopes or combinations of these chemicals. Artificial particles such as latex beads may be labeled with organic chemical reactions, enzymatic coupling, covalent modification or osmotic incorporation of the label to the bead. Natural particles may be labeled by these same methods and also by biosynthetic labeling, encapsulation, physical manipulation, hydrophobic or hydrophilic interactions, conjugation, ionic interaction or combinations of these methods. These labeled particles can be detected with appropriate detectors. Labeled particles are adhered to the surface, such as by sedimentation or assisted sedimentation (e.g. centrifugation), and label detected from the adhered particles to determine the adhesion of the surface. Adhesion may be determined from parameters related to adhesion such as Fadh, $K_H$ or from the PIF value determined for the particles.

Surfaces which may be tested include any solid surface to which cells will adhere even if only slightly. This includes glass, ceramic, metal and preferably, plastic such as plastic tissue culture products. Optionally, surfaces or particles may be modified or pre-treated with process or agents which affect adhesive properties. This type of treatment is helpful for indicating how and where to modify a particle or surface to increase or decrease its adhesiveness. Treatments which may be used to modify adhesiveness include chemical treatments, enzymatic treatments, physical treatments, treatment with electromagnetic radiation such as x-rays or ultraviolet rays, thermal (heat or cold) treatments and combinations of these treatments. Surfaces or particles may also be coated with substances designed or suspected to increase or decrease overall stickiness or smoothness. Coatings may comprise antibodies, cytokines, enzymes, recombinant proteins, matrices, adhesion molecules, lipids, polysaccharides, synthetic polymers and combinations of these substances.

Adherence to surfaces is important in many applications including growing cells in culture where the purpose is to maintain cell attached to the surface or, alternatively, to avoid cell attachment. Surfaces may also be tested to determine the degree of stickiness to other substances such as metals, algae, sludge and microorganisms. Stickiness of a surface is an important consideration in the design and construction of, for example, plumbing at waste and water treatment facilities and in manufacturing. These methods are useful in determining the overall stickiness of nearly any product and can also be used in quality control procedures to determine product smoothness or the overall condition of a surface.

The following examples illustrate embodiments of the invention, but should not be viewed as limiting the scope of the invention.

EXAMPLES

Example 1

Cell Cultures.

Human umbilical vein (HUV) endothelial cell cultures were grown as described by S. Kourembanas et al. (J. Clin. Invest. 86:670–74, 1990). These HUV cells, were passed 4–6 times, grown to confluence on 10 cm cell cultures dishes, dispersed with trypsin, washed and plated at a density of approximately $5 \times 10^5$ cells/well onto 96-well, flat-bottom microtiter plates (Nunc; Naperville, Ill.). Cultures were confluent in 24 hours and used in adhesion experiments.

Cell cultures of JY, an Epstein-Barr virus-transformed human B cell line, and Jurkat, a human T cell leukemia line, were maintained in DMEM supplemented with 10% Newborn Calf serum (NCS; Sigma Chemical; St. Louis, Mo.), 2 mM L-glutamine, 100 units/ml of penicillin and 100 ug/ml of streptomycin (Gibco/BRL; Grand Island, N.Y.) at 37° C. in a humidified 5% $CO_2$ atmosphere. Human neutrophils and Ficoll-Hypaque density gradient centrifugation fraction of mononuclear cells were purified as described by I. Ginis and A. I. Tauber (Blood, 76:1233–39, 1990). Monocytes were separated using a homotopic human monocyte aggregation assay (S. J. Mentzer et al., Cell. Immunol. 101:101–08, 1986). All leukocytes were immediately resuspended at $2 \times 10^6$ cells/ml and labeled with 2 uM of 2'-7'-bis (carboxyethyl)-5-(and 6)carboxy-fluorescein acetoxymethyl ester ("calcein-AM"; Molecular Probes; Eugene, Oreg.) for 20 minutes at 37° C., washed and resuspended in Earle's Balanced Salt Solution containing 0.25 mM Hepes (EBSS/Hepes).

Example 2

Coating Plates with Extracellular Matrix (ECM) Proteins.

All proteins were purchased from Sigma Chemical (St. Louis, Mo.). 96 well plates were coated with fibronectin, vitronectin, both from human plasma, human placenta collagen type IV or mouse sarcoma basement membrane laminin as described by J. Fehr et at. (J. Clin. Invest. 76:535, 1985). 10 ug/ml of these proteins were suspended in phosphate buffer saline (PBS) and added to the microtiter wells for one hour at room temperature. The wells were washed three times with PBS and used immediately.

Example 3

Adhesion Centrifugation Assay.

Microtiter wells coated with confluent monolayers of endothelial cells or ECM proteins were washed once with EBSS/Hepes. One hundred uls of calcein labeled leukocytes resuspended in EBSS/Hepes were added to each well and allowed to adhere for 30 minutes at 37° C. and 5% $CO_2$ (I. Ginis et al., Am. J. Physiol. 264:617–26, 1993; I. Ginis et al., J. Cell. Physiol. 157:569–78, 1993). In blocking experiments utilizing antibodies, monoclonal antibodies were added first to endothelial cell monolayers followed with neutrophils. Fluorescence intensity of plated cells was read on a CytoFluor 2300 Plate Scanner (Millipore; Bedford, Mass.) at excitation and emission wavelengths of 485 and 530 nm, respectively.

Non-adherent leukocytes were removed by gentle washing the plates three times with 200 ul of EBSS/Hepes, prewarmed to 37° C. In some experiments the plates, along with adherent cells, were sealed with transparent plastic (Dynatech Diagnostics; South Windham, Me.), inverted and centrifuged at 100×g and the fluorescence of the remaining adherent cells read again and compared to initial fluorescence. Background fluorescence of the medium alone was measured separately for each plate and subtracted from all readings. Each experiment was performed in triplicate or quadruplicate. The standard deviation (SD) of repetitive readings was less than 30% of the mean. Leukocyte adhesion to endothelial cell monolayers was also monitored by fluorescent cell microscopy to exclude homotopic aggregation of neutrophils in the well.

Example 4

Fluorescence of Cell Suspension.

Cells loaded with fluorescent dye were added to a 96 well plate, evenly suspended within a certain volume of medium (FIG. 1), and the plate scanned with a fluorescent plate scanner. Light signal from a single cell in suspension detected by the scanner depends on extinction properties of the medium and on the distance between the cell and the fluorescence detector. In the arrangement depicted in FIG. 1A, the detector is located at the bottom of the plate. According to the Beer-Lambert law for monochromatic light the emitted (fo) and detected (f) fluorescence values for each cell are related by the following equation:

$$\ln\left(\frac{fo}{f}\right) = Eh \text{ or } f = fo \times e^{-Eh}, \tag{1}$$

where E is a coefficient characterizing extinction properties of the medium and h is the distance from the cell to the light detector. By integrating equation (1) over the total volume of the medium containing N cells, the following relationship between the detected fluorescence of cell suspension (Fsusp) and the genuine, emitted fluorescence Fo (Fo=N×fo) of these cells can be determined:

$$F_{susp} = \int_0^H N \times \frac{fo}{H} \times e^{-Eh}dh, \text{ or } F_{susp} = Fo \times \frac{1-e^{-EH}}{EH} \quad (2)$$

Figure 1B:
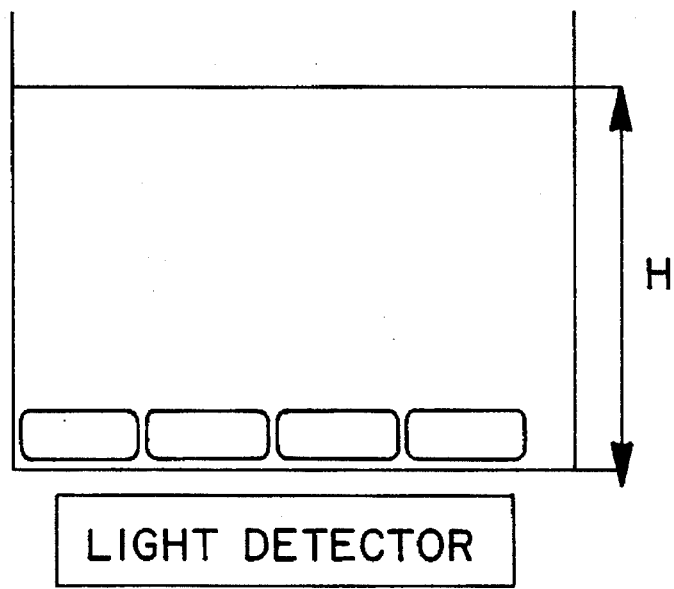

As the volume of the cell suspension is decreased, the detected fluorescence, Fsusp, approaches the emitted fluorescence, Fo. In the ideal, theoretical case, when all the cells are completely flattened on the bottom of the well, the emitted and the detected fluorescence will become identical (FIG. 1B).

$$\lim_{H \to 0} F_{susp} = \lim_{H \to 0} \left( Fo \times \frac{1-e^{-EH}}{EH} \right) = Fo \quad (3)$$

Expression (2) shows that detected and emitted fluorescence values of the cell suspension are interrelated by the multiplier:

$$K_H = \frac{1-e^{-EH}}{EH} \quad (4)$$

According to expression (4), $K_H$ is determined only by the extinction properties of the medium and the volume of the cell suspension in the well, and does not depend on cell number, cell size or the amount of fluorescent dye loaded in the cells. Determination of $K_H$ was accomplished by measurement of the fluorescence of certain numbers of cells reSuspended in different volumes of medium (FIG. 2).

Figure 2:
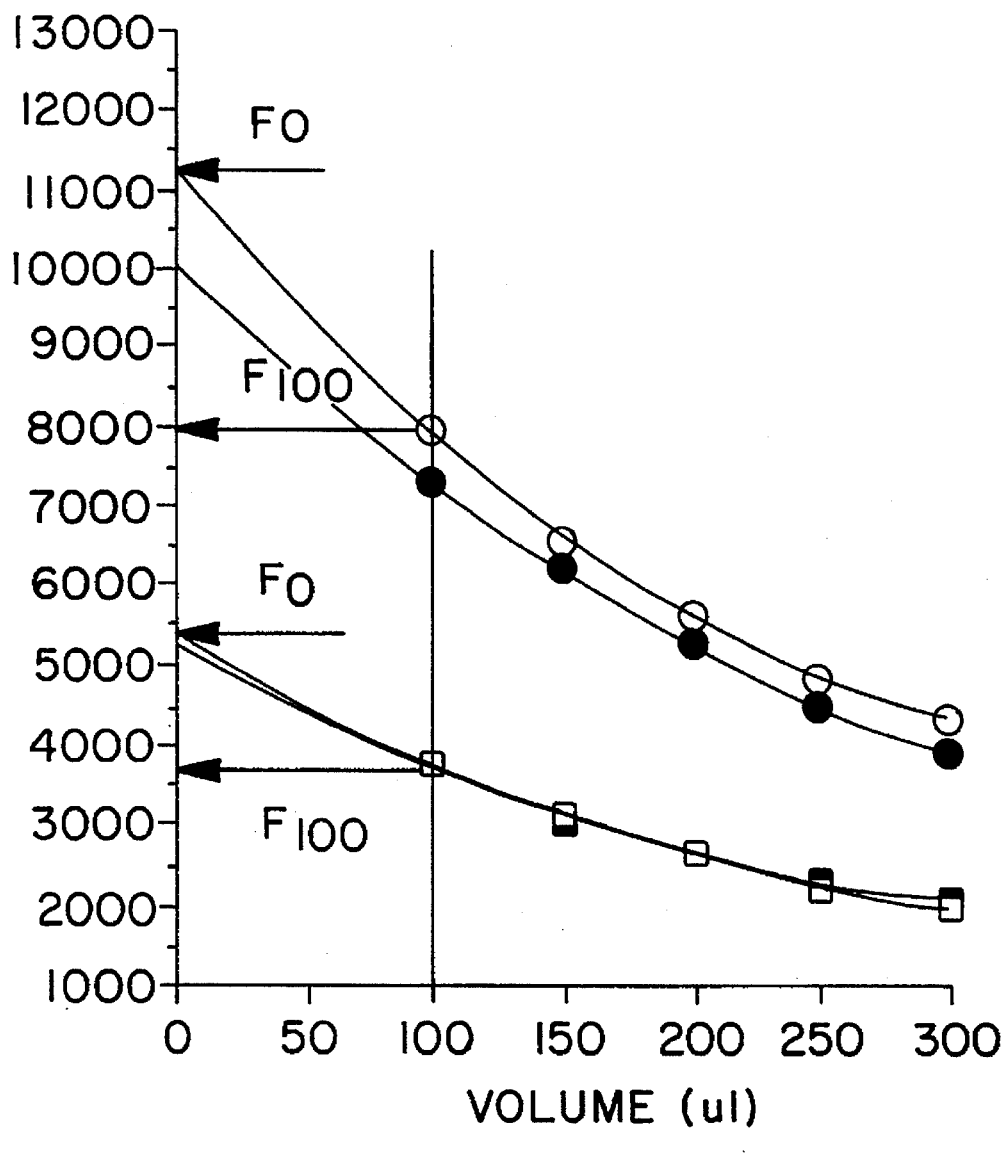
FIG. 2 Detected fluorescence of a constant number of cells as a function of volume of medium in which the cells are suspended.

Detected fluorescence of a constant number of cells, as a function of volume of medium in which the cells were suspended, was determined (FIG. 2). $10^5$ or $2\times10^5$ neutrophils loaded with fluorescent dye (calcein), were resuspended in increasing volumes of DMEM and added to a 96-well plate. Plates were scanned using CytoFluor 3500 Millipore plate scanner (Millipore; Bedford, Mass.). Regardless of the number of cells in each well ($10^5$/well in the first experiment or $2\times10^5$/well in the second experiment), the fluorescence signal detected by the scanner varied as a function of the volume in which the cells were suspended. In all cases there was no difference between the fluorescence of evenly suspended cells and cells which had been lysed with detergent, releasing the fluorescent dye into solution.

Figure 3:
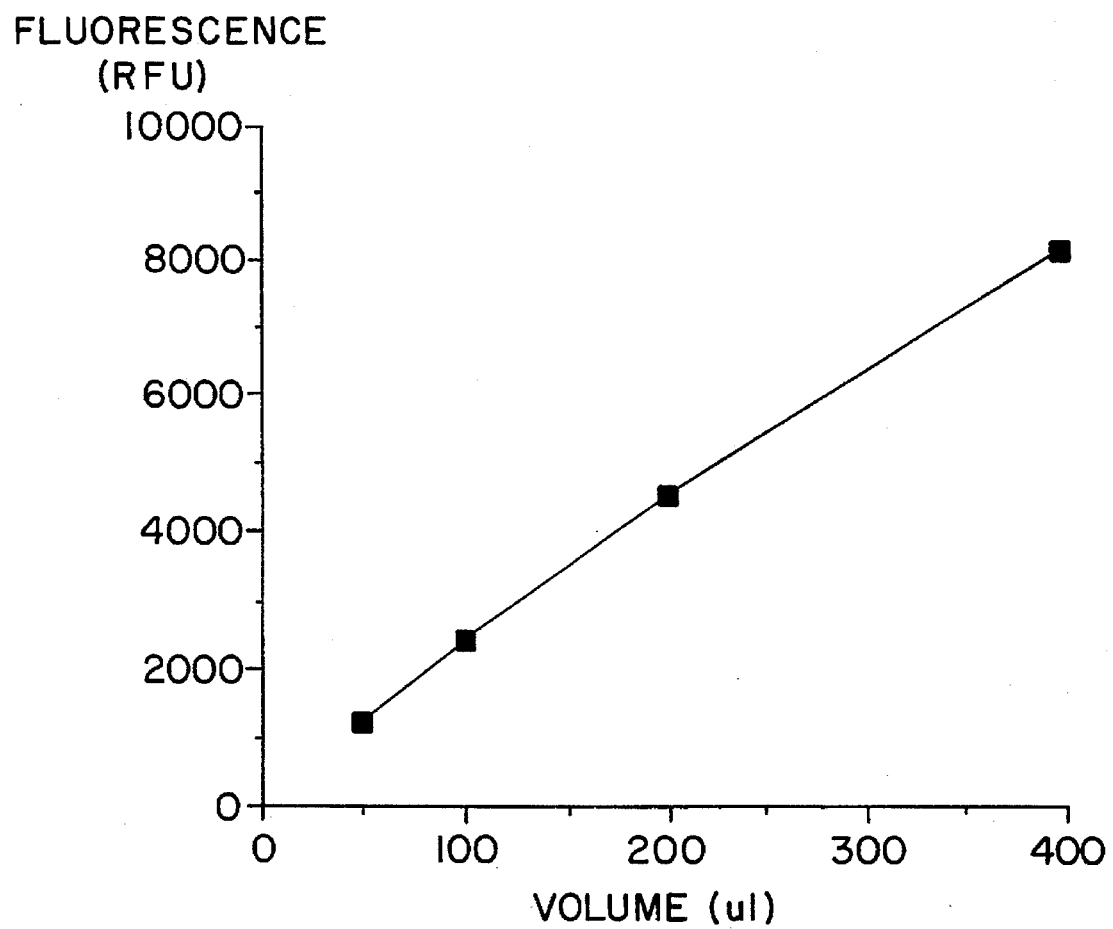
FIG. 3 Detected fluorescence of increasing volumes of cell suspension.

To show that the decrease of the detected fluorescence was actually the result of the extinction of the emitted fluorescence and not of the optical limitations of the scanner, two control experiments were performed. First, increasing volumes of a suspension of neutrophils loaded with fluorescent dye, calcein, and resuspended at $10^6$/ml in DMEM were plated onto a 96-well plate and scanned. As shown in FIG. 3, there is a linear relationship between the total number of cells in the well and detected fluorescence, demonstrating that the plate scanner is able to detect fluorescence from all the cells in the well and even those suspended at the top of the well.

Figure 4B:
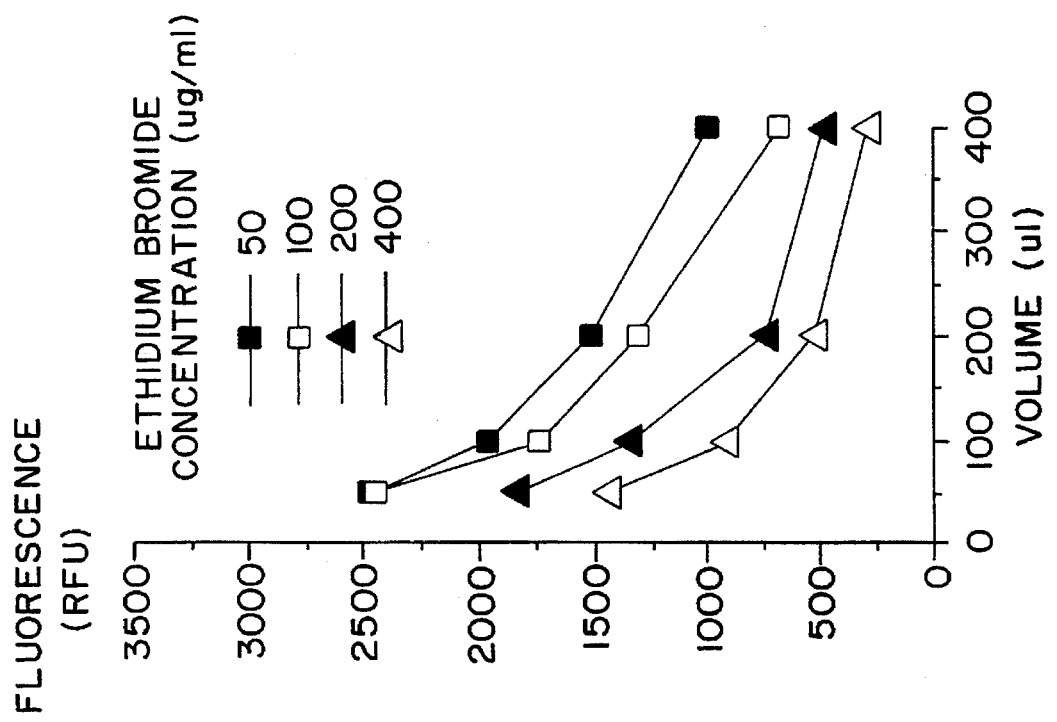
FIG. 4 Fluorescence extinction properties of media containing A phenol red or B ethidium bromide.
Figure 4A:
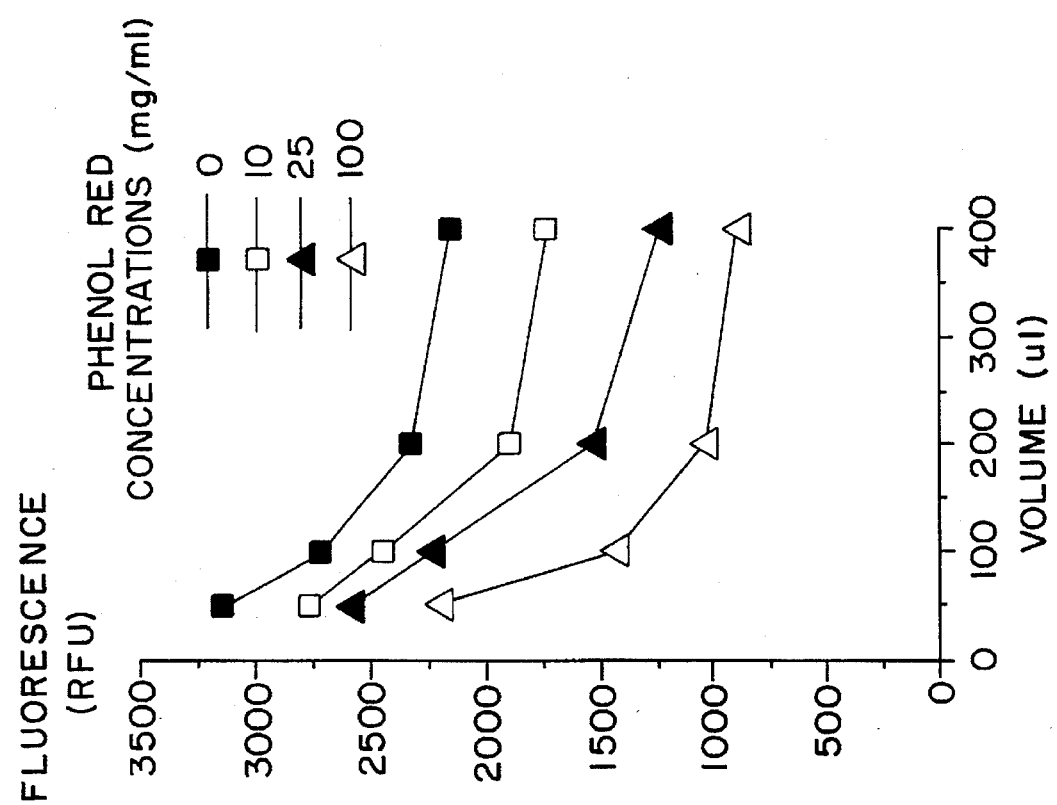
Figure 5:
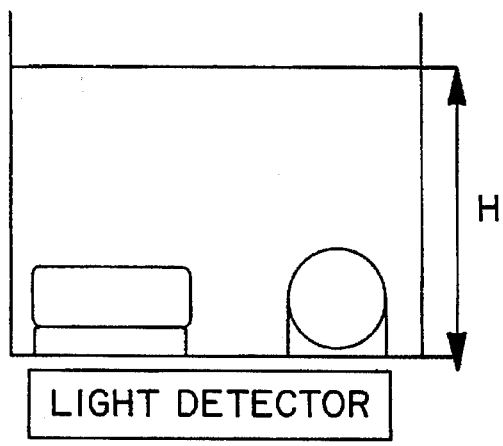
FIG. 5 Adherent cell and cell surface separation distances.

Second, media with different optical extinction properties were used to suspend the same number of neutrophils as in the experiment described above. $10^5$ neutrophils, loaded with fluorescent dye, were resuspended in increasing volumes of phenol red (FIG. 4A) or ethidium bromide (FIG. 4B) solutions in PBS, added to a 96-well plate and scanned. Cells were resuspended in DMEM tissue culture medium, which contains phenol red as a pH indicator. Because phenol red has peak of absorption at 555 nm, which overlaps with emission spectrum of calcein (peak at 530 nm), it was assumed that phenol red was responsible for the extinction properties of DMEM. Suspending the neutrophils in the buffer containing varying concentrations of phenol red demonstrated that the detected fluorescence of calcein-labeled PMN depended on the concentration of phenol red in the dilution buffer. The same relative effects were observed using ethidium bromide instead of phenol red. The peak of absorption of ethidium bromide (535 nm) is also close to calcein emission peak.

Example 5

Calculating Fo and $K_H$.

There are two methods of calculating Fo and $K_H$ using the experimental data shown on FIG. 2. In the first method, using exponential curve fit and regression analysis (Cricket Graph), Fsusp is described as a function of volume by extrapolating to zero in experimental curves of absolute fluorescence values (FIG. 2). Once Fo was calculated, $K_H$ was determined for a certain volume of cell suspension (100 uls or $K_{100}$) according to equation (4).

This experiment was performed using several different types of cells. Exponential fluorescence values of the 100 ul/well volume of cell suspensions and corresponding extrapolated values of Fo were substituted in the equation (4), and $K_H$ values for the 100 ul/well ($K_{100}$) were calculated. The results obtained are summarized in Table 1 which demonstrates $K_{100}$ values for neutrophils and peripheral blood lymphocytes plated at two different concentrations and also for fluorescently labeled polystyrene beads.

TABLE 1

| $K_{100}$ Values for Different Cell Types | | | |
|---|---|---|---|
| Type of Cells | | $F_{100}$ | Fo | $K_{100} = F_{100}/Fo$ |
| PMN | $1 \times 10^{-5}$ | 1275 | 1700 | 0.7500 |
| PMN lysed | $1 \times 10^{-5}$ | 1175 | 1600 | 0.7344 |
| PMN | $2 \times 10^{-5}$ | 3460 | 4700 | 0.7362 |
| PMN lysed | $2 \times 10^{-5}$ | 3310 | 4300 | 0.7700 |
| PBL | $1 \times 10^{-5}$ | 703 | 950 | 0.7400 |
| PBL lysed | $1 \times 10^{-5}$ | 788 | 1000 | 0.7880 |
| PBL | $2 \times 10^{-5}$ | 1380 | 1940 | 0.7113 |
| PBL lysed | $2 \times 10^{-5}$ | 1520 | 2080 | 0.7308 |
| beads | $2 \times 10^{-5}$ | 1910 | 2550 | 0.7490 |

All cell types were resuspended in increasing volumes of DMEM and the ratio between the detected fluorescence and the extrapolated emitted fluorescence was calculated. PMN= neutrophils; PBL=peripheral blood lymphocytes; beads= fluorescently labeled polystyrene beads. $K_{100}$ was approximately 0.74 for all cell types. This result confirms theoretical predictions from the equation (4), demonstrating that $K_H$ does not depend on cell type or cell concentration. Cell suspension and lysed cells both have the same $K_H$, indicating that the plate scanner sees a cell suspension as a homogeneous solution of the dye and disregards cell size.

The second method requires only two experimental values of Fsusp: detected fluorescence of a certain volume of cell suspension ($F_H$) and detected fluorescence of a double of this volume ($F_{2H}$). Substituting $F_H$ and $F_{2H}$ in equation (2) provides a system of equations:

$$\left. \begin{array}{l} F_H = Fo \times \dfrac{1-e^{-EH}}{EH} \\[6pt] F_{2H} = Fo \times \dfrac{1-e^{-E2H}}{E2H} \end{array} \right\} \quad (5)$$

This system, can be solved to determine Fo and E:

$$Fo = \frac{(F_H)^2 \times \ln\frac{2 \times F_H - F_H}{F_H}}{2 \times (F_{2H} - F_H)} \quad (6)$$

$$E = \frac{1}{H} \times \ln\frac{F_H}{2 \times F_{2H} - F_H} \quad (7)$$

Substituting $F_H$ and $F_{2H}$ in equation (6) for detected fluorescence of 100 ul/well and 200 ul/well volumes of cell suspensions described in Table 1, Fo and $K_{100}$ values for these suspensions can also be calculated. Fo values were very close to those obtained by curve extrapolation and $K_{100}$ was equal to 0.69±0.07 (mean±SD). $K_{100}$ values for the cells resuspended in the buffer containing increasing concentrations of phenol red and ethidium bromide (FIGS. 4A and 4B) decreased from 0.75 to 0.43 and from 0.75 up to 0.63, respectively. Calculation of extinction coefficient E using equation (7) is also useful, as this coefficient includes all ingredients of the dilution medium and extinction properties of the microtiter plate.

Example 6

Detected Fluorescence of an Adherent Cell.

An adherent cell is close to the bottom of the plate, and thus, close to the detector. It is not still an ideally flattened cell and there is some distance between much of the adherent cell and the surface of adhesion. A solution of light-absorbing reagent which fills the space between adherent cells loaded with fluorescent dye and a surface of adhesion, will quench the fluorescent light emitted by the cells. Knowing the quenching factor $K_H$ for suspended cells, the PIF value of the adherent cells can be calculated. PIF is a percent ratio of the detected fluorescence of adherent cells (F adherent) to the absolute emitted fluorescence of these cells (Fo):

$$PIF = \frac{Fadh}{Fo} \times 100\% \quad (8)$$

To determine PIF a simple two-step protocol was designed and utilized. First, cells were allowed to adhere onto the bottom of the wells in 96-well plate. Non-adherent cells were washed out and adherent cells were covered with 100 uls of a light-absorbing solution. The plated was scanned by a fluorescent plate reader to measure detected fluorescence of adherent cells (F adherent or Fadh).

Second, adherent cells were lysed by addition of small amounts of detergent, and the plate scanned again to measure fluorescence of the same cells as if they were not adherent, but rather suspended all over the volume of the well (F suspended or Fsusp). Knowing Fsusp and the quenching factor $K_{100}$ ($K_{100}$ for DMEM was 0.7) PIF can be calculated. PIF reflects the distance between adherent cells and the surface of adhesion, and thus, the degree of cell spreading on the surface.

Example 7

Verification of the Method for Different Adhesion Models.

There are at least three components in any adhesion assay: adherent cells, surface of adhesion, and external factors such as time, stimuli, or adhesion inhibitors such as monoclonal antibodies against adhesion receptors. PIF was found to change in a predictable manner after varying each of these components.

a) Effect of the Type of Adherent Cell on PIF Values

Leukocytes were loaded with fluorescent dye and allowed to adhere for 30 min at 37° C. to human umbilical vein (HUV) endothelial cell monolayers previously plated onto 96 well plate. Nonadherent cells were removed by washing 3 times with EBSS/Hepes. PIF values were determined as described above.

TABLE 2

Leukocyte-HUV Monoclonal Antibody Adhesion

| Cell Type | PIF (mean ± sem) |
|---|---|
| Neutrophils | 81.95 ± 2.7% |
| Monocytes | 71.47 ± 4.3% |
| PBL | 70.23 ± 3.0% |
| Jurkat T cells | 66.32 ± 3.4% |
| JY B cells | 66.26 ± 6.9% |

Neutrophils had the highest PIF values and Pals, which do not spread significantly upon adhesion, had significantly lower PIF values as is the case also with lymphocyte cell-lines.

b) Effects of Different Surfaces PIF Values.

Figure 6:
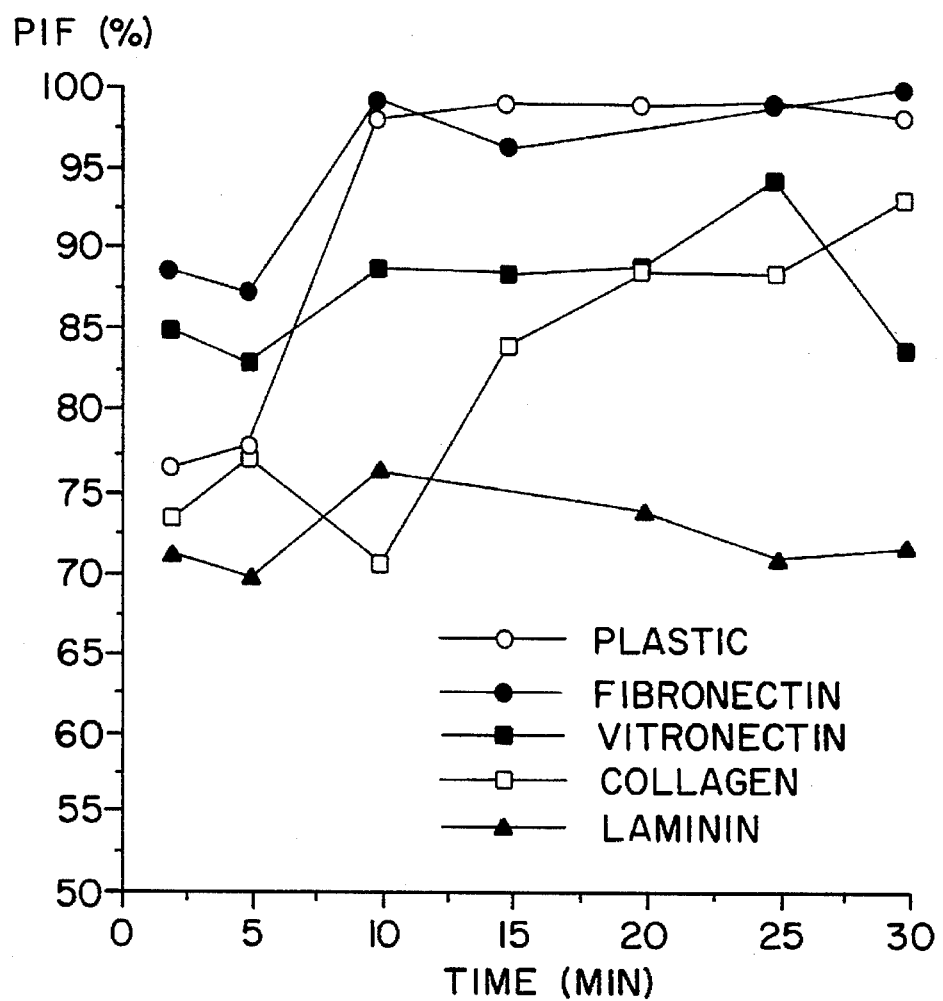
FIG. 6 Graphic comparison of PIF values for neutrophils adherent to different surfaces.

ECM proteins allow for different degrees of spreading (E. M. Hemlet, Ann. Rev. Immunol. 8:365–400, 1990). Uncoated plastic, fibronectin, and vitronectin are known to promote spreading. PIF as a function of time for neutrophils adherent to different ECM protein-coated and uncoated plastic was tested. Neutrophils loaded with calcein were allowed to adhere for 5 minutes to (A) vitronectin or (B) laminin coated well plates (FIG. 6). Nonadherent cells were removed by centrifugation and cellular morphology was determined using fluorescent microscopy. Neutrophils were also loaded with fluorescent dye and allowed to adhere for various times at 37° C. to 96 well plate coated with different ECM proteins. To remove non-adherent cells, the plate was sealed, inverted and centrifuged 2 minutes at 1,000 rpm at 4° C. Determination of PIF was performed according to the two-step protocol described above.

Neutrophils are known to have high spreading potential. Neutrophils adherent to plastic, fibronectin or vitronectin demonstrated a very high PIF, while those adherent to laminin had the lowest PIF. These results are consistent with morphological observations. Most of the neutrophils adherent to vitronectin are already spread by 5 minutes, while neutrophils adherent to laminin exhibited much less spreading.

c) Effect of External Factors on PIF Values

Neutrophils loaded with calcein were allowed to adhere to HUV endothelial cells in the presence of 25 ng/ml of PMA for 15 minutes. Non-adherent cells were removed by centrifugation and PIF measurements were performed according to the two-step protocol described above. HUV endothelial cells were incubated for 4 hours in the presence of 25 units of IL-1/ml washed twice and incubated for 30 minutes with calcein-loaded resting neutrophils. Non-adherent cells were removed by centrifugation and PIF measurements were performed according to the two-step protocol described above. The PIF of neutrophils adherent to HUV monolayers previously treated with IL-1 was consistently increased (Table 3).

TABLE 3

Effect of Activation of Adhesion Counterparts On Neutrophils or Endothelial Cell PIF Values.

| Treatment | PIF (mean ± sem) | p values |
|---|---|---|
| none | 81.95 ± 2.7% (7) | |
| PMA | 93.50 ± 2.6% (3) | 0.05 |
| IL-1 | 91.60 ± 1.2% (3) | 0.006 |

Leukocytes loaded with calcein were allowed to adhere to unstimulated endothelial cells in the presence or absence of monoclonal antibody TS1/22 (10 ug/ml) for 30 minutes at 37° C. TS1/22 is an $IgG_1$ directed against CD11a α chain and was purified from hybridoma ascites fluid (S. J. Mentzer and D. V. Faller, Exper. Hematol. 18:812–17, 1990). Non-adherent cells were removed by rinsing 3 times with 200 uls of EBSS/Hepes and PIF measurements were performed according to the two-step protocol described above.

TABLE 4

Effect of Anti-LFA-1 Monoclonal Antibody (TS1/22) on PIF Values

| | PIF (mean ± sem) | | |
|---|---|---|---|
| Cells Type | Control | TS1/22 | p Value |
| neutrophils | 82.76 ± 4.9 (8) | 68.01 ± 3.12 | 0.0124 |
| lymphocytes | 78.77 ± 5.9 (4) | 65.01 ± 4.41 | 0.0197 |
| Monocytes | 75.52 ± 3.4 (5) | 66.73 ± 2.73 | 0.0276 |

When human leukocytes, neutrophils and lymphocytes were allowed to adhere to HUV endothelial cells in the presence of TS1/22, their PIF values were significantly decreased as compared to adhesion in the absence of anti-LFA-1 (Table 4).

Example 8

Correlation of Cell Spreading with Apoptosis.

Figure 7:
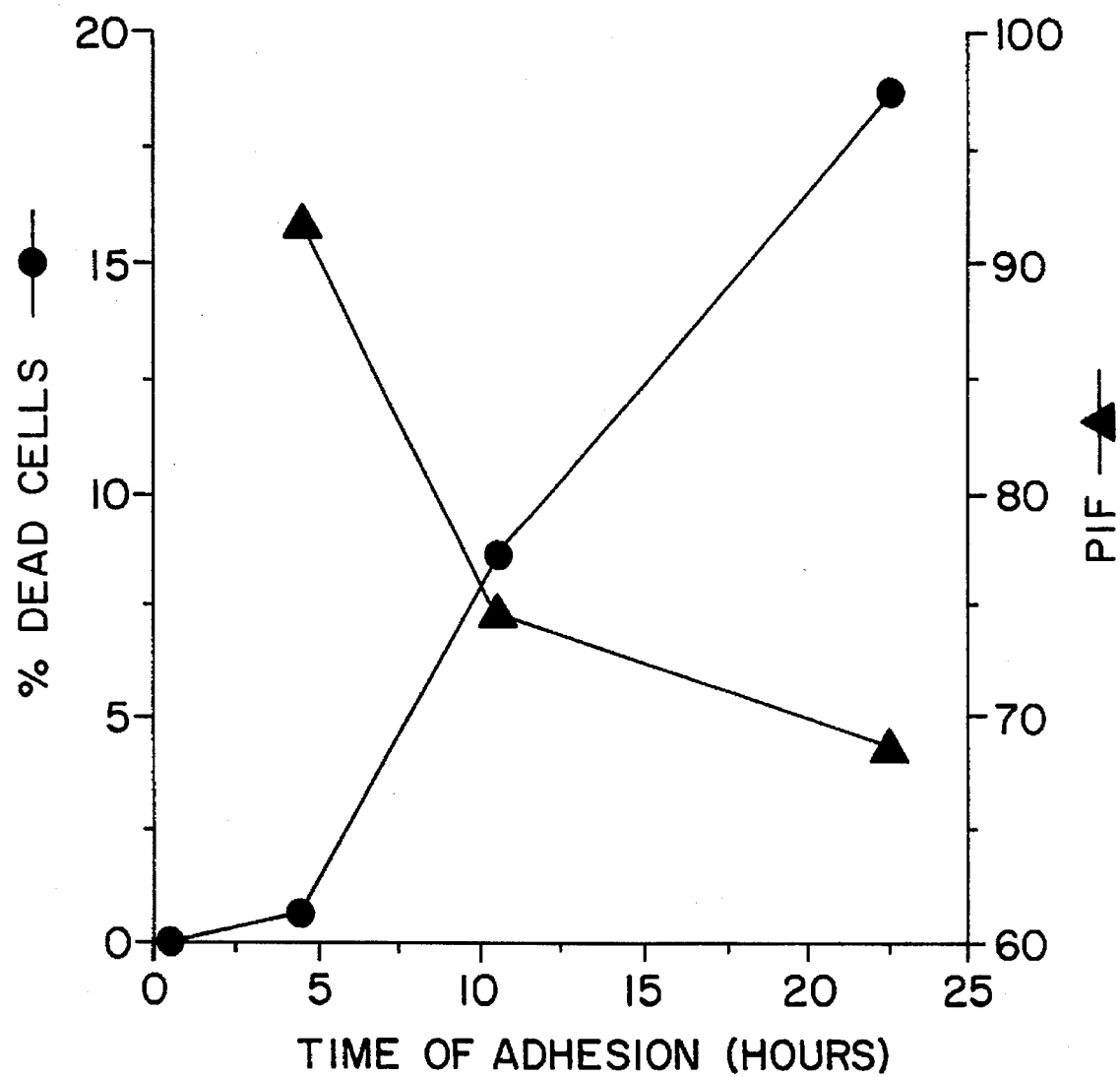
FIG. 7 Graphic depiction of PIF values for neutrophils adherent to plastic in relation to apoptosis over time.
Figure 8A:
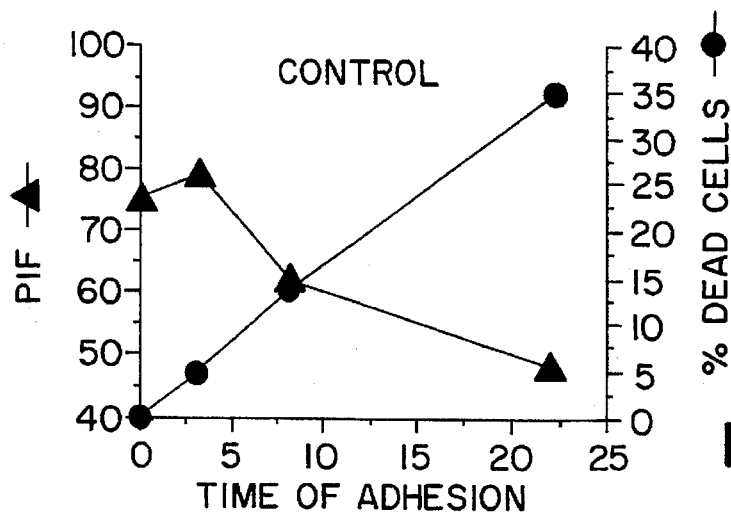
FIG. 8 Graphic depiction of PIF values for neutrophil-endothelial cell adhesion in relation to apoptosis over time: (A) control cells; (B) FMLP activated cells; and (C) IL-1 activated cells.
Figure 8B:
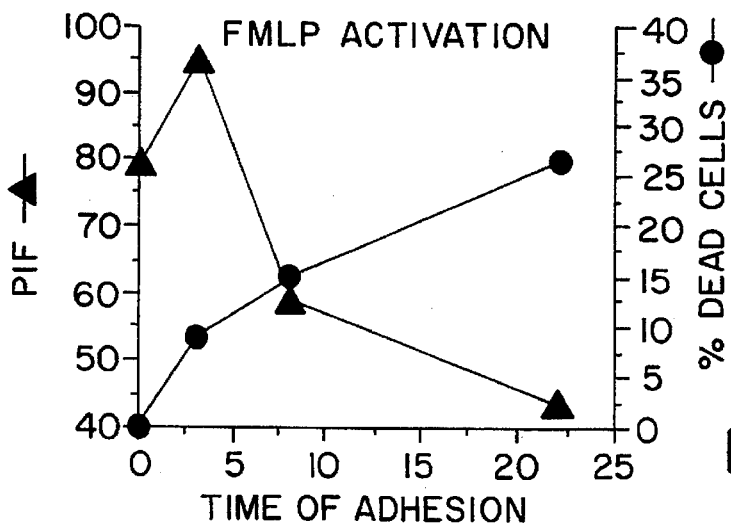
Figure 8C:
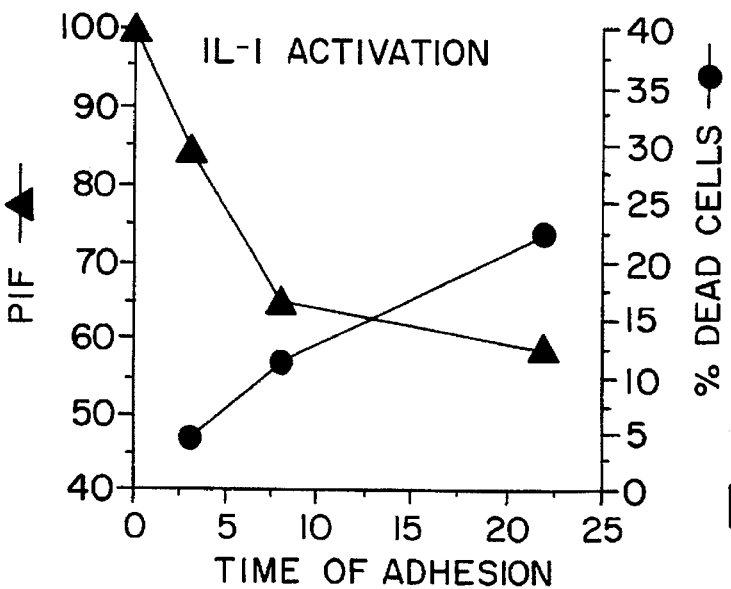

Neutrophils, some of which were activated with IL-1 or FMLP, were simultaneously labeled with calcein (yellow fluorescence) for adhesion and spreading assays, and with propidium iodide homodimer (red fluorescence) for dead cell measurements. Labeled neutrophils were plated in a 96-well plate (FIG. 7) or a plate coated with endothelial cells (FIG. 8) and the amount of fluorescence measured on CytoFluor using different filters to estimate the number of dead cells in the wells. Non-adherent cells were washed out and the plate read again. Results indicated that dead cells did not adhere. Cells which did adhere exhibited PIF values inversely proportional to the number of dead cells in the initial measurement. As the number of dead cells is presumed to reflect the number of cells undergoing apoptotic changes leading to cell death, apoptotic cells are less capable of spreading. These results indicate that cell spreading may be useful as a means for analyzing the physiological state of a population of cells.

Example 9

Identification and Isolation of Abnormal Cells using PIF Values.

Microtiter wells coated with confluent monolayers of endothelial cells or ECM proteins are washed once with EBSS/Hepes. One hundred uls each (about $10^5$ cells) of calcein labeled normal leukocytes, cytomegalovirus-infected leukocytes and transformed leukocytes are suspended in EBSS/Hepes, added individually to wells of a microtiter plate and allowed to adhere for 30 minutes at 37° C. and 5% $CO_2$. Fluorescence intensity of plated cells is read on a CytoFluor 2300 Plate Scanner (Millipore; Bedford, Mass.) at excitation and emission wavelengths of 485 and 530 nm, respectively. Non-adherent leukocytes are removed by gentle washing of the plates, three times, with 200 ul of EBSS/Hepes, prewarmed to 37° C. Plates with adherent cells are sealed with transparent plastic (Dynatech Diagnostics; South Windham, Me.), inverted and centrifuged at 100×g and the fluorescence of the remaining adherent cells read again and compared to initial fluorescence. Background fluorescence of the medium alone is measured separately for each plate and subtracted from all readings. Each experiment is performed in triplicate or quadruplicate. PIF values are determined as described and compared. Each is expected to give a characteristic PIF value. Consistency is tested using different sources of cells, different types of infections and different transformed cells. Results are accumulated, recorded and maintained to create a chart of PIF values verses cell type. Infected, transformed or otherwise abnormal cells may be characterized by comparison to known values of the chart.

Example 10

Measurements of Cellular Adhesion on Tissue Culture Surfaces.

Neutrophils are obtained by Ficoll-Hypaque density gradient centrifugation of heparinized blood. Cells are immediately resuspended in 2 uM of calcein-AM and incubated for 20 minutes at 37° C. After incubation, the cells are washed in PBS and resuspended in ice-cold EBSS/Hepes at $2\times10^6$ cells/ml. One hundred ul samples are placed into wells of three different types of 96-well tissue culture plates, previously washed once with PBS and once with EBSS/Hepes. Plate "N" (Nunc; Naperville, Ill.); Plate "G" (GIBCO/BRL; Grand Island, N.Y.); Plate "S" (Schleicher & Schuell, Inc.; Keene, N.H.); Plate "M" (Millipore; Bedford, Mass.).

Cells are allowed to adhere to the wells for 30 minutes at 37° C. in a 5% $CO_2$ humidified atmosphere. Nonadherent cells are removed by gently washing the plates three times with 200 ul EBSS/Hepes; prewarmed to 37° C. Plates are scanned using a CytoFluor 3500 Millipore plate scanner (Millipore; Bedford, Mass.). Background fluorescence is measured separately for each plate and subtracted from all readings to obtain Fadh. To the wells is added a small amount of detergent which lyses the cells and the plates are scanned again. As before, background is subtracted out, but this time to obtain Fsusp. Knowing $K_H$ and Fsusp for the cells, Fo is determined according to equation (4). PIF is calculated according to equation (8). Plates with increased PIF values have a higher degree of cellular adhesion for the cells tested and very likely for most other cells as well. These results demonstrate that the surface conditions of most any material can be analyzed and the information obtained immediately used to increase product quality.

Example 11

Identification of Antibodies that Affect Cell Spreading or Adhesion.

Figure 9:
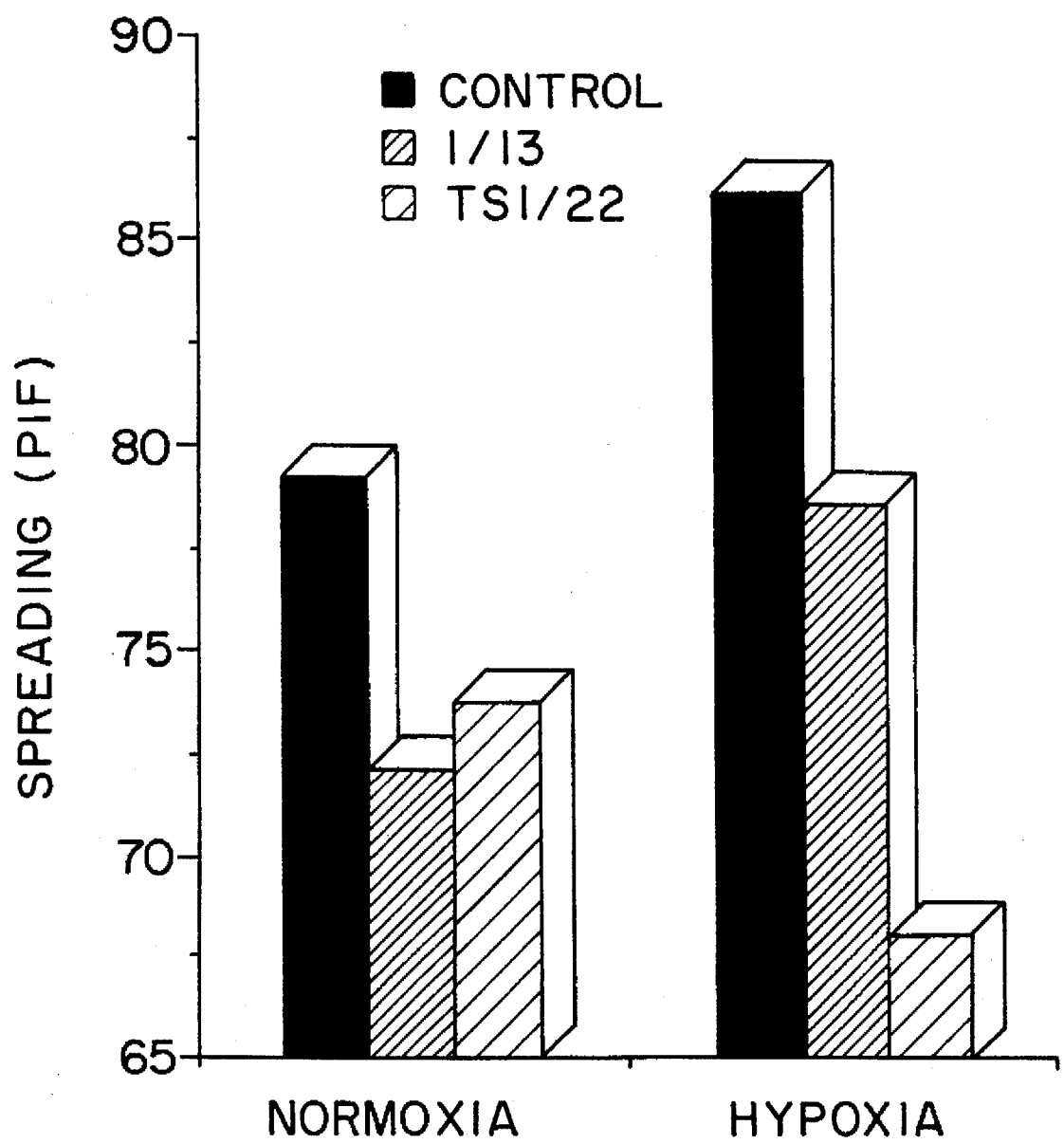
FIG. 9 Graphic depiction of the amount of cell spreading, as determined with PIF values, which occurred with antibody treated normoxic and hypoxic endothelial cells.

Human neutrophils were obtained by Ficoll-Hypaque density gradient centrifugation and immediately resuspended at $2\times10^6$ cells/ml in 2 uM calcein-AM. Cells were incubated for 20 minutes at 37° C., washed and resuspended in EBSS/Hepes. Microtiter wells coated with confluent monolayers of HUV endothelial or control cells, were subjected to hypoxic environment, washed once with EBSS/Hepes, and 100 ul/well of calcein-labeled neutrophil suspension added to each well. Cells were adhered for 30 minutes at 37° C. and 5% $CO_2$. Monoclonal antibodies directed either against the neutrophil integrin reporter LFA-1 (TS1/22) or against the undefined adhesion receptor on endothelial cells (1/13) were added together with neutrophils. Non-adherent leukocytes were removed by centrifugation of the sealed and inverted plates at 100×g, and the fluorescence of the remaining adherent cells was read. Adherent neutrophils were lysed using 1% SDS and fluorescence measured again. PIF values were calculated according to the method described above. Background fluorescence (medium alone) was measured separately for each plate and subtracted from all readings. Each experiment was performed in triplicate or quadruplicate. The standard deviation (SD) of repetitive readings was less than 30% of the mean. The profile depicted in FIG. 9 is representative of multiple experiments and demonstrates that monoclonal antibody 1/13 had an inhibitory effect on neutrophil spreading on both, normoxic and hypoxic endothelial cells. This effect was comparable to that of the monoclonal antibody directed against neutrophil integrin, LFA-1, known to mediate strong neutrophil adhesion and spreading. These results indicate that the adhesion ligand, which is recognized by monoclonal antibody 1/13 is similar to LFA-1 in a way that it also participates in neutrophil spreading on endothelial cells. These results demonstrate that these methods can be used to screen and isolate the function or actions of unknown agents such as antibodies by virtue of their effect on cellular spreading and adhesion.

Other embodiments and uses of the invention will be apparent to those skilled in the art from consideration of the specification and practice of the invention disclosed herein. It is intended that the specification and examples be considered exemplary only, with the true scope and spirit of the invention being indicated by the following claims.

We claim:

1. A method for measuring cellular adhesion comprising the steps of:
    a) labeling a population of cells with a detectable label and suspending the labeled cells in a liquid medium;
    b) dividing the suspended cells into a plurality of wells wherein each well contains a comparable number of cells and a different volume of medium;
    c) detecting label from the wells of suspended cells;
    d) calculating a function for label detected verses volume of medium;
    e) calculating a quenching factor ($K_H$) of the medium from the function;
    f) adhering the suspended cells to well surfaces; and
    g) detecting label from the wells of adhered cells and, from the label detected and the quenching factor, measuring cellular adhesion in the population of cells.

2. The method of claim 1 wherein the population of cells is selected from the group consisting of circulating cells, cells of the immune system, cells of the hematopoietic system, human cells, endothelial cells, neoplastic cells, immortalized cell lines, infected cells and combinations thereof.

3. The method of claim 1 wherein the detectable label is selected from the group consisting of florescent chemicals, luminescent chemicals, phosphorescent chemicals, chromatic chemicals, metals, radio isotopes, stable isotopes and combinations thereof.

4. The method of claim 1 wherein the label is detected after cells are subjected to electromagnetic radiation.

5. The method of claim 4 wherein the electromagnetic radiation is selected from the group consisting of gamma rays, x-rays, ultraviolet rays, visible light, infrared rays, microwaves, radio waves, electric fields and combinations thereof.

6. The method of claim 1 wherein the liquid medium is selected from the group consisting of cell culture mediums, buffered solutions, ionically balanced solutions and combinations thereof.

7. The method of claim 1 wherein the liquid medium is phosphate buffered saline.

8. The method of claim 1 wherein the wells are in a microtiter plate.

9. The method of claim 1 wherein the wells are coated with a protein selected from the group consisting of fibronectin, vitronectin, collagen, laminin and combinations thereof.

10. The method of claim 1 wherein label is detected by a detector placed below the wells.

11. The method of claim 1 wherein the suspended cells are adhered to well surfaces by centrifugation.

12. The method of claim 1 wherein cellular adhesion is measured as percent of ideal flattening.

13. The method of claim 1 further comprising the steps of binding a ligand to the surface of the labeled cells and measuring cellular adhesion in the population of ligand-bound cells.

14. The method of claim 13 wherein the ligand is selected from the group consisting of antibodies, antigens, enzymes, cytokines, pharmaceutical agents, recombinant gene products and combinations and fragments thereof.

15. The method of claim 1 further comprising the step of pre-treating the population of cells and measuring cellular adhesion in the population of pre-treated cells.

16. The method of claim 15 wherein the pre-treatment is selected from the group consisting of treatments with electromagnetic radiation, thermal treatments, chemical treatments, treatments with a pharmaceutical composition, enzymatic treatments, treatments with a cytokine and combinations thereof.

17. The method of claim 1 further comprising the step of detecting a pathological disorder in the population of cells by comparing cellular adhesion measured for the population of cells with cellular adhesion measured for a similar population of cells.

18. The method of claim 17 wherein the pathological disorder detected is selected from the group consisting of neoplasias, inflammations, immune system disorders, infections, cardiac diseases, hematopoietic system disorders and genetic defects and deficiencies.

19. The method of claim 17 wherein the similar population of cells comprises normal or diseased cells of the same tissue-type and species as the population of cells.

20. A method for determining a distance between a population of cells and a surface to which the cells are adhered comprising the steps of:
    a) labeling the population of cells with a detectable label and suspending the labeled cells in a liquid medium;
    b) dividing a portion of the suspended cells into a plurality of wells wherein each well contains a different number of cells and a comparable volume of medium;
    c) detected label from the plurality of wells;
    d) lysing the cells in the plurality of wells;
    e) detecting label from the lysed plurality of wells;

f) calculating a function of label detected from lysed and unlysed cells verses cell number;

g) calculating a quenching factor ($K_H$) of the medium from the function;

h) dividing another portion of the suspended cells into another plurality of wells;

i) adhering said another portion of the suspended cells to the surface of the wells; and j) detecting label from the wells of adhered cells and, from the label detected and the quenching factor, determining the distance between the population of cells and the surface to which the cells are adhered.

21. The method of claim 20 wherein the population of cells is obtained from a diseased patient.

22. The method of claim 20 wherein the cells are adhered to well surfaces before being lysed.

23. The method of claim 20 wherein the cells are lysed by the addition of a detergent.

24. The method of claim 23 wherein the detergent is selected from the group consisting of anionic, cationic, zwitterionic and non-ionic detergents.

25. A method for determining surface adhesion comprising the steps of:

a) labeling a collection of particles with a detectable label and suspending the labeled particles in a fluid medium with a known or determinable quenching factor;

b) adhering the labeled particles to the surface; and c) measuring label detected from the adhered particles and, from the label detected and the quenching factor, determining surface adhesion.

26. The method of claim 25 wherein the surface is selected from the group consisting of ceramics, glasses, plastics, metals, biological surfaces and combinations thereof.

27. The method of claim 25 wherein the surface is a tissue culture product.

28. The method of claim 25 wherein the particles are selected from the group consisting of beads, crystals, liposomes, artificial cells and biological cells.

29. The method of claim 25 wherein labeling is performed by a process selected from the group consisting of organic chemical reactions, enzymatic labeling, biosynthetic labeling, hydrophobic interaction, ionic interaction, conjugation, covalent modification and osmotic incorporation.

30. The method of claim 25 further comprising the step of treating the surface before adhering said particles.

31. The method of claim 25 wherein the treatment is selected from the group consisting of chemical treatments, enzymatic treatments and combinations thereof.

32. The method of claim 25 wherein the treatment is selected from the group consisting of physical treatments, treatments with electromagnetic radiation, heat treatments and combinations thereof.

33. A method for measuring adhesion of particles comprising the steps of:

a) labeling the particles with a detectable label and suspending the labeled particles in a fluid;

b) dividing the suspended particles into a plurality of samples wherein each sample contains a different number of particles in a comparable volume of fluid;

c) detecting label from the samples;

d) calculating a function for label detected verses particle number;

e) calculating a quenching factor ($K_H$);

f) adhering the suspended particles to a surface; and g) detecting label from the adhered particles and, from the label detected and the quenching factor, measuring adhesion.

34. The method of claim 33 wherein the particles are selected from the group consisting of beads, crystals, liposomes, artificial cells and biological cells.

35. The method of claim 33 wherein the particles are coated.

36. The method of claim 35 wherein the coating is selected from the group consisting of antibodies, cytokines, enzymes, recombinant proteins, matrices, adhesion molecules, lipids, polysaccharides, synthetic polymers and combinations thereof.

37. The method of claim 33 wherein the detectable label is selected from the group consisting of florescent chemicals, luminescent chemicals, phosphorescent chemicals, chromatic chemicals, metals, radio isotopes, stable isotopes and combinations thereof.

38. The method of claim 33 wherein the surface is selected from the group consisting of ceramics, glasses, plastics, metals, biological surfaces and combinations thereof.

39. The method of claim 33 wherein the particles are labeled by a process selected from the group consisting of organic chemical reactions, encapsulation, ionic interactions, hydrophobic interactions, covalent modifications, conjugations, osmotic incorporation, physical manipulations and combinations thereof.

* * * * *